US011123376B2

(12) United States Patent
Wallace et al.

(10) Patent No.: US 11,123,376 B2
(45) Date of Patent: Sep. 21, 2021

(54) METHOD OF TREATMENT

(71) Applicants: HUDSON INSTITUTE OF MEDICAL RESEARCH, Clayton (AU); MONASH UNIVERSITY, Clayton (AU)

(72) Inventors: Euan Wallace, Clayton (AU); Rebecca Lim, Cranbourne North (AU)

(73) Assignees: MONASH UNIVERSITY, Clayton (AU); HUDSON INSTITUTE OF MEDICAL RESEARCH, Clayton (AU)

( * ) Notice: Subject to any disclaimer, the term of this patent is extended or adjusted under 35 U.S.C. 154(b) by 63 days.

(21) Appl. No.: 15/735,817

(22) PCT Filed: Jun. 10, 2016

(86) PCT No.: PCT/AU2016/050468
§ 371 (c)(1),
(2) Date: Dec. 12, 2017

(87) PCT Pub. No.: WO2016/197196
PCT Pub. Date: Dec. 15, 2016

(65) Prior Publication Data
US 2019/0336539 A1    Nov. 7, 2019

(30) Foreign Application Priority Data

Jun. 12, 2015 (AU) .............................. 2015902214
Apr. 12, 2016 (AU) .............................. 2016901349

(51) Int. Cl.
*A61K 35/50* (2015.01)
*A61P 11/00* (2006.01)
*A61P 9/10* (2006.01)

(52) U.S. Cl.
CPC ............... *A61K 35/50* (2013.01); *A61P 9/10* (2018.01); *A61P 11/00* (2018.01)

(58) Field of Classification Search
None
See application file for complete search history.

(56) References Cited

U.S. PATENT DOCUMENTS

2014/0010801 A1   1/2014   Niedernhofer et al.
2014/0294840 A1   10/2014   Bullerdiek et al.

FOREIGN PATENT DOCUMENTS

| CN | 104382827 | 3/2015 |
| CN | 104666344 A | 6/2015 |
| WO | WO 2008144820 | 12/2008 |

OTHER PUBLICATIONS

Asea, et al. (2008) "Heat shock protein-containing exosomes in mid-trimester amniotic fluids", Journal of Reproductive Immunology, 79: 12-17.*
Vakhshiteh, et al. (2019) "Mesenchymal stem cell exosomes: a two-edged sword in cancer therapy", International Journal of Nanomedicine, 14: 2847-59.*
Wu, et al. (2016) "Exosomes in Parkinson's Disease", Neuroscience Bulletin, 33(3): 331-38.*
Vella, et al. (2016) "Focus on Extracellular Vesicles: Exosomes and Their Role in Protein Trafficking and Biomarker Potential in Alzheimer's and Parkinson's Disease" International Journal of Molecular Sciences, 17(2): 173 (e-article), pp. 1-20.*
Tan, et al. (2018) "Aminion Epithelial Cell-Derived Exosomes Restrict Lung Injury and Enhance Endogenous Lung Repair", Stem Cells Translational Medicine, 7: 180-96.*
Ambalavanan, et al. (2016) "Searching for better animal models of BPD: a perspective", American Journal of Cell and Molecular Biology, 211: L924-27.*
Matute-Bello, et al. (2008) "Animal models of acute lung injury", AJP Lung Cell Mol Physiol, 295: 379-99.*
Kotton, et al. (2001) "Bone marrow-derived cells as progenitors of lung alveolar epithelium", Development, 128(24): 5181-88.*
Gutteridge, et al. (1994) "Transient iron overload with bleomycin detectable iron in the plasma of patients with adult respiratory distress syndrome", Thorax, 49: 707-710.*
Qui, et al. (2003) "Arrest of B16 Melanoma Cells in the Mouse Pulmonary Microcirculation Induces Endothelial Nitric Oxide Synthase-Dependent Nitric Oxide Release that is Cytotoxic to the Tumor Cells", American Journal of Pathology, 162(2): 403-12.*
Mei, et al. (2007)"Prevention of LPS-Induced Acute Lung Injury in Mice by Mesenchymal Stem Cells Overexpressing Angiopoietin 1", PLoS Medicine, 4(9): 1525-37.*
Uchida, et al. (2000) "Neurotrophic Function of Conditioned Medium From Human Amniotic Epithelial Cells", Journal of Neuroscience Research, 62: 585-90.*
Brown, et al. (2005) "Neurodegenerative Diseases: An Overview of Environmental Risk Factors", Environmental Health Perspectives, 113(9): 1250-56.*
Murphy, "Human Amnion Epithelial Cells Do Not Abrogate Pulmonary Fibrosis in Mice with Impaired Macrophage Function" Cell Transplantation, vol. 21, p. 1477-1492, 2012.
Keller, "Exosomes: From biogenesis and secretion to biological function", Immunology Letters, vol. 107, p. 102-108, 2006.
Urbanelli, "Exosome-based strategies for diagnosis and therapy" Recent Patents on CNS Drug Discovery, vol. 10, No. 1, p. 10-27, 2015.
Chinese Office Action cited in Application No. 201680047646.2 dated Sep. 27, 2020.
Tingfen Li et al., Exosomes derived from human umbilical cord mesenchymal stem cells alleviate liver fibrosis, Stem Cells Dev., vol. 22, No. 6, pp. 845-854.
Asea et al., Journal of Reproductive Immunology, vol. 79, No. 1, pp. 12-17.
Chinese Office Action cited in 201680047646.2 dated May 18, 2021.

* cited by examiner

*Primary Examiner* — Robert M Kelly
(74) *Attorney, Agent, or Firm* — Workman Nydegger

(57) ABSTRACT

The present disclosure relates generally to the methods of treatment of mammalian subjects by an enhanced cell-based therapeutic approach in order to facilitate tissue and neuronal repair, regeneration and/or reparation. Medicaments useful in the treatment of mammalian subjects and methods of production of the medicaments are also encompassed by the present disclosure.

7 Claims, 20 Drawing Sheets

A

B

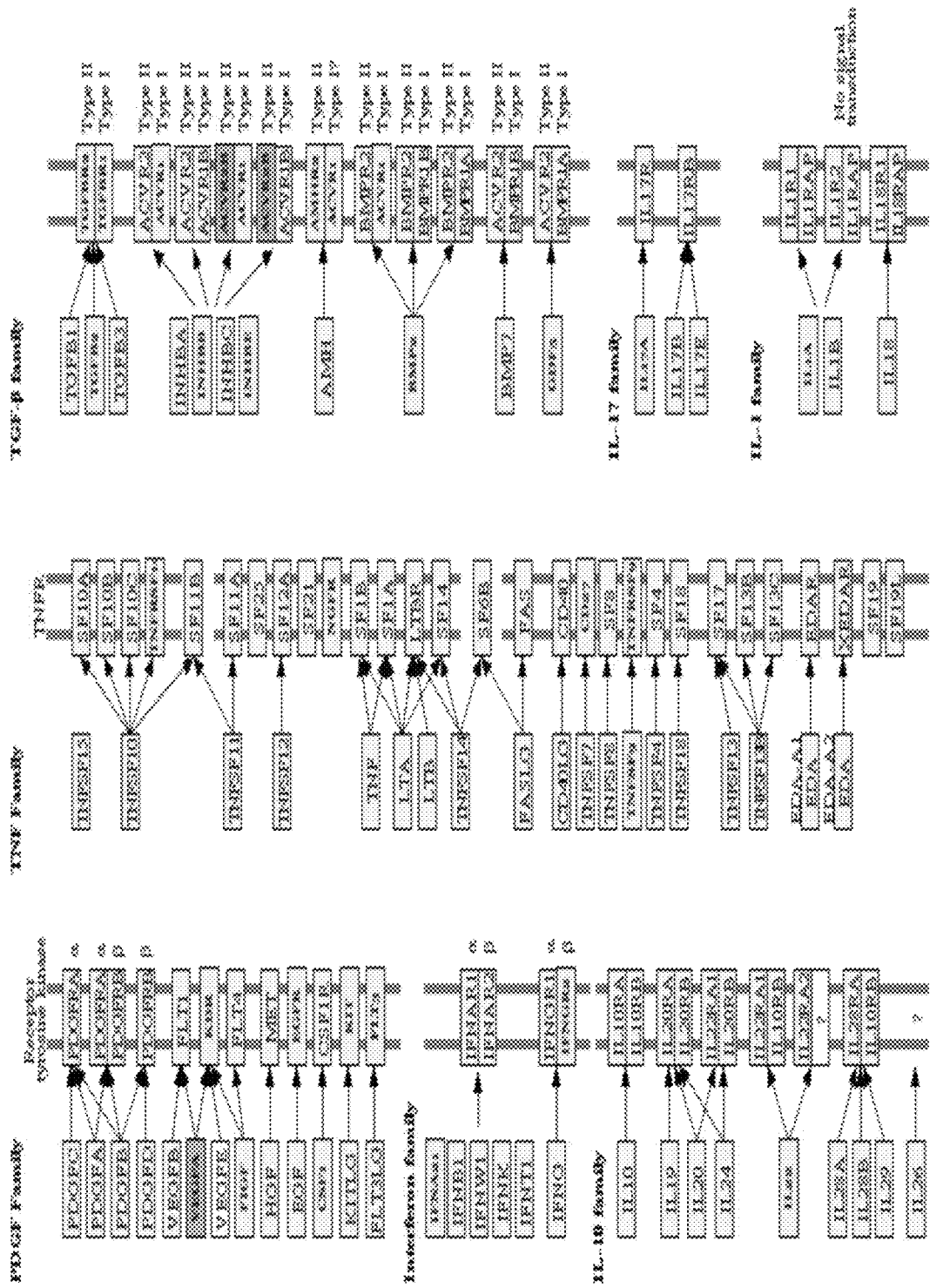

METHOD OF TREATMENT

This application is associated with and claims priority from Australian Provisional Patent Application No. 2015902214, filed on 12 Jun. 2015, entitled "A method of treatment" and Australian Provisional Patent Application No. 2016901349, filed on 12 Apr. 2016, entitled "A method of treatment", the entire contents of which, are incorporated herein by reference.

BACKGROUND

Field

The present disclosure relates generally to the methods of treatment of mammalian subjects by an enhanced cell-based therapeutic approach in order to facilitate tissue and neuronal repair, regeneration and/or reparation. Medicaments useful in the treatment of mammalian subjects and methods of production of the medicaments are also encompassed by the present disclosure.

Description of Related Art

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Modern medicine has been greatly advanced by the identification of chemical therapeutics and biologic agents such as antibiotics. However, many medicaments have multifactorial functions, some influencing off-target physiological effects. Cell-based therapeutics have been proposed as the next pillar of modern medicine (Fishback et al. (2013) *Sci Transl Med* 5:179 ps7).

One of the rate limiting factors in cell-based therapies is the potential for inconsistent product. This is highlighted in trials involving stem cells. Mesenchymal stem cells (MSCs), for example, whilst well characterized in the literature and have achieved clinical trial level, generally require serial passaging for use. This can and frequently does adversely impact on when and how the cells can be used.

One approach to counter this problem has been to use banked mesenchymal progenitor cells. This at least avoids the delay between harvest and therapy. However, this introduces a variability in potency of the cells between donors and does not address the issue of the negative impact of serial passaging.

An interim measure to address this issue is to have a "master" cell bank. Again, this does not overcome the inevitable problem that there is a finite number of passages that the cells can undergo before senescence and epigenetic/karyotypic changes occur (Schellenberg et al. (2011) *Aging* (Albany N.Y.) 3: 873-888). There is also a risk of immune rejection after repeated doses.

As a case in point, with marked improvements in obstetric surveillance and neonatal care, an increasing number of premature babies survive resulting in an elevation in the prevalence of "diseases of prematurity". One particularly debilitating condition is bronchopulmonary dysplasia (BPD) which is an incurable chronic lung disease of very preterm infants. It is characterized by maldevelopment and arrest of alveoli and disruption of the pulmonary capillary architecture. BPD is a major case of morbidity and mortality in new born children. Survivors of BPD are also at serious risk of obstructive respiratory disease in early adulthood (Doyle et al, (2006) *Paediatrics* 118: 108-113) and of general chronic ill health and cognitive decline (Lodha et al. (2014) *PLoSONE*: e90843). Whilst mesenchymal stem cells have been proposed as a possible cell-based therapy for BPD, for the reasons outlined above, there are likely batches of cells with widely differing functional effectiveness which, apart from causing emotional stress, may delay other therapeutic choices.

The issue of damage to pulmonary capillary architecture is not only confined to human preterm infants. The animal racing industry and in particular the horse racing industry faces the problem of exercise induced pulmonary haemorrhage (EIPH). In some jurisdictions, a horse, for example, which exhibits a nose bleed more than twice after racing is banned for life from further competition. This can result in devastating economic losses. A chemical therapeutic approach to preventing or treating EIPH is likely to cause ethical concerns in terms of performance enchantment and in any event such an approach is unlikely to regenerate burst capillaries.

The beneficial effects of human amnion epithelial cells (hAECs) have been documented (for examples, Hodges et al. (2012) *Am J Obstet Gynerol* 206: 448e8-448e15; Murphy et al. (2012) *Cell Transplant I*: 1477-1492; Vosdoganes et al. (2013) *Cytotherapy* 15:1021-1029; Yawno et al. (2013) *Dev Neurosci* 35:272-282). However, there is a need to determine their mechanism of action.

It is clear, therefore, that the problem of cell-based therapies needs to be addressed and an alternative strategy is required.

SUMMARY

In accordance with the present invention a vesicular vehicle for cellular communication is identified as being released from mammalian amnion epithelial cells (AECs). The vesicles, referred to herein as "amniotic exosomes", are nanometer-sized extracellular vesicles (50-100 nm) derived from late endosomes and released from cell surfaces.

Taught herein is an improved form of mammalian amnion epithelial cell-based therapy. The improvement comprises the use of the nano-sized amniotic exosomes which are released by the epithelial cells and exert reparative effects by activating endogenous repair mechanisms. Amniotic exosomes are shown herein to act directly on immune cells to inter alia reduce T-cell proliferation, increase macrophage phagocytosis, activate stem cells and inhibit collagen production in activated fibroblasts. It is proposed herein that the amniotic exosomes release a profile of exosomal cargo in the form of proteins (e.g. cytokines) and genetic molecules (e.g. miRNA, mRNAs and non-coding RNAs).

The biogenesis of exosomes involves the formation of intraluminal vesicles by the inward budding of the late endosome's limiting membrane. Late endosomes then fuse with the plasma membrane to release the exosomes. Once secreted, exosomes can either be taken up by target cells located in close proximity to the parent cell or travel to distal sites through the circulation. Mechanistically, exosomes operate as complex vectors that contain parental cell material. They can contain proteins and genetic material, which are then transferred to their target cells.

The present invention is predicated, therefore, on the development of an enhanced approach to cell-based therapy. The present disclosure teaches the use of the amniotic exosomes which are released from mammalian amnion epithelial cells and which have immunomodulatory, pro-regenerative and reparative effects. The amniotic exosomes exert an effect on immune cells to reduce T-cell proliferation, increase macrophage phagocytosis and activate endogenous stem cells through the release of beneficial proteomic and genetic molecules such as miRNA, mRNA and non-coding RNAs. The amniotic exosomes are proposed herein to facilitate tissue repair, regeneration and reparation including wound healing, promote cellular maintenance, induce neuronal protection including ameliorating the effects of neurodegeneration and injury and promoting repair and neuroregeneration. The amniotic exosomes, also suppress collagen production in activated fibroblasts. The exosomes are further proposed to promote repair and regeneration following disease or adverse event in the systemic vasculature such as ischemic reperfusion injury or organ damage including ameliorating kidney, liver, pancreas, heart and lung damage as well as the treatment of fibrotic conditions in those organs (e.g. liver or lung fibrosis). The exosomes are also useful in promoting myelination and hence are proposed to be useful in the treatment of demyelination diseases or disorders such as multiple sclerosis.

The amniotic exosomes have beneficial effects not only in humans but also non-human mammals. Hence, the present invention extends to human and veterinary applications. AECs from human subjects are referred to herein as "hAECs".

An example of a veterinary application is the treatment of racing animals including horses, racing dogs and camels for exercise induced pulmonary haemorrhage (EIPH).

The amniotic exosomes can be produced in large quantity by culturing mammalian amnion epithelial cells in a bioreactor and isolating the amniotic exosomes from the conditioned culture medium. The epithelial cells can be maintained as an immortalized cell line. The amniotic exosomes can be isolated when required or stored in a lyophilized state.

An innovative feature of the present invention is that it is not necessary to identify a compatible donor of the mammalian amnion epithelial cells in order to use the amniotic exosomes. The exosomes do not induce an adverse immunological reaction. Rather, donors are selected on the basis of gestational stage and/or other characteristics such as health of a neonate or term babies. In an embodiment, however, the amniotic exosomes are derived from hAECs from patients at the terminal end period of a pregnancy. The amnion epithelial cells produce amniotic exosomes which are at least as good at promoting tissue or neuronal repair, regeneration and/or reparation for different physiological conditions as are amnion epithelial cells. However, there is none of the disadvantages of a cell-based therapy. Hence, an aspect of the present invention is donor selection in order to identify amnion epithelial cells which produce amniotic exosomes useful in treating a desired condition. This can lead to the generation of a bank of amnion epithelial cells. A particular batch of cells can then be selected based on the disease or condition to be treated.

Pharmaceutical compositions comprising the amniotic exosomes, therapeutic kits comprising amniotic exosomes and/or reagents for screening for a suitable donor or amnion epithelial cell line and bioreactor kits are also encompassed by the teachings of the present disclosure.

Taught herein is an enhanced or modified form cell-based therapy. Hence, enabled herein is an improved cell-based therapeutic protocol for treating a mammalian including a human subject by the use of amnion epithelial cells the improvement comprising isolating amniotic exosomes from an immortalized amnion epithelial cell line and systemically or locally administering to the subject in need of tissue or neuronal repair, regeneration and/or reparation including promotion of remyelination.

BRIEF DESCRIPTION OF THE FIGURES

Some figures contain color representations or entities. Color photographs are available from the Patentee upon request or from an appropriate Patent Office. A fee may be imposed if obtained from a Patent Office.

hAEC total exo total MSC exo (Anderson et al. (2016) Stem cells http://doi.ory/10.1002/stem.2298).

Figure 18:
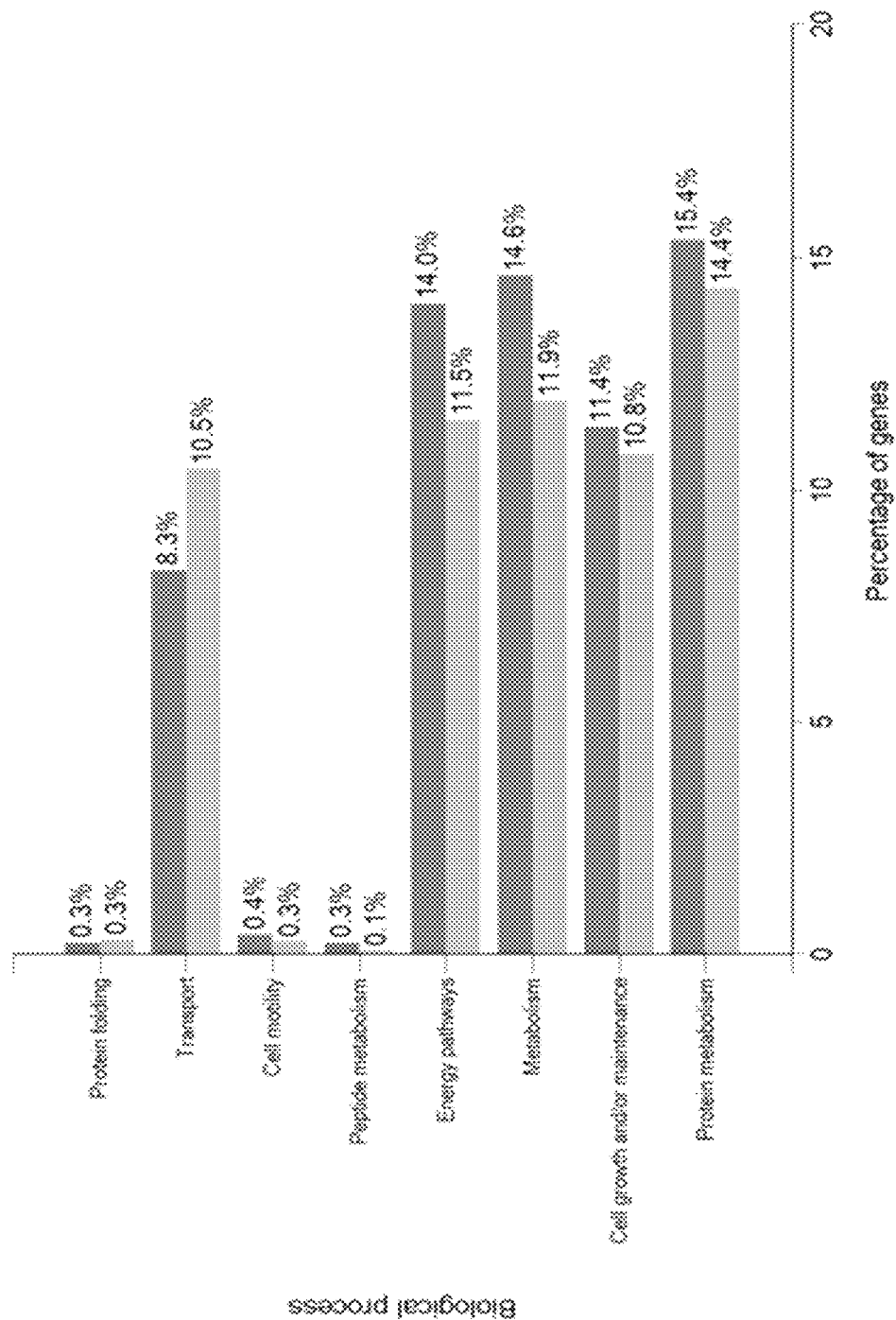

FIG. 18 is a graphical representation of a biological process comparison between hAEC and total MSC (Anderson et al. (2016) supra).

hAEC total exo total MSC exo (Anderson et al. (2016) supra).

DETAILED DESCRIPTION

Throughout this specification, unless the context requires otherwise, the word "comprise" or variations such as "comprises" or "comprising", will be understood to imply the inclusion of a stated element or integer or method step or group of elements or integers or method steps but not the exclusion of any element or integer or method step or group of elements or integers or method steps.

As used in the subject specification, the singular forms "a", "an" and "the" include plural aspects unless the context clearly dictates otherwise. Thus, for example, reference to "a disease or condition" includes a single disease or condition, as well as two or more diseases or conditions; reference to "an exosome" includes a single exosome, as well as two or more exosomes; reference to "the disclosure" includes a single and multiple aspects taught by the disclosure; and so forth. Aspects taught and enabled herein are encompassed by the term "invention". A "disease" or "condition" also includes a "disorder". All such aspects are enabled within the width of the present invention. Any variants and derivatives contemplated herein are encompassed by "forms" of the invention.

The present disclosure teaches an enhanced cell-based therapy to facilitate the treatment of mammalian subjects for a range of diseases and conditions falling generally within the context of repair, regeneration and reparation of cells, tissues, neurological pathways and endocrine pathways. The present disclosure teaches that amniotic exosomes isolated from conditioned medium used to culture mammalian amnion epithelial cells (AECs) have beneficial immunomodulatory physiological and biochemical properties. In essence, the mammalian amniotic exosomes exert an effect on immune cells to reduce T-cell proliferation, increase macrophage phagocytosis and activate endogenous stem cells through the release of proteomic and genetic molecules such as miRNA, mRNA and non-coding RNA. They also suppress collagen production in activated fibroblasts. Importantly, the amniotic exosomes are not immunogenic and hence, allogeneic amniotic exosomes can be used.

The amniotic exosomes also reverse established lung inflammation and lung fibrosis and reverse activation of primary lung fibroblasts. This also applies to fibrosis of other organs such as the liver, pancreas, heart and kidney. In addition, they contain miRNAs, mRNAs and non-coding RNA, that target cytokine-cytokine receptor signaling pathways, Wnt signaling pathways, PI3K-Akt signaling pathways and TGFβ signaling pathways as well as signaling pathways involved in a diverse range of physiological and neurological processes.

The present specification teaches that the mammalian amniotic exosomes induce repair, regeneration and reparation of cells, tissues including organs, neurological pathways, components of the systemic vasculature as well as promoting wound healing. It is proposed herein that the amniotic exosomes facilitate repair, regeneration and reparation of the brain and spinal cord, promote repair of neuroregenerative conditions, induce reparation of organ damage following trauma, disease or substance abuse, facilitate repair following stroke or other insult to the brain such as traumatic brain injury. The exosomes are proposed to facilitate remyelination in the treatment of a demyelination disease, condition or disorder such as multiple sclerosis, optic neuritis, Devic's disease, transverse myelitis, acute disseminated encephalomyelitis and adrenoleukodystrophy and adrenomyeloneuropathy. The amniotic exosomes in an embodiment, facilitate repair of lung damage. This is important in the treatment of bronchopulmonary dysplasia (BPD) in human babies. It also has veterinary application in the treatment of exercise induced pulmonary haemorrhage (EIPH) in racing animals such as horses, racing dogs (e.g. greyhounds) and camels.

Accordingly, the present invention enabled herein is a method of treating a mammalian subject, the method comprising the systemic or local administration of mammalian amniotic exosomes derived from allogeneic mammalian amnion epithelial cells from a donor mammal of the same species.

Reference to a "mammalian subject" includes any mammal requiring treatment. In an embodiment the mammalian subject is a human. The term "AEC" means "amniotic epithelial cell". When from a human, the AECs are designated "hAECs".

Hence, the present specification in instructional on a method for treating a human subject, the method comprising the systemic or local administration of human amniotic exosomes derived from allogeneic human amnion epithelial cells from a human donor.

In another embodiment, the mammalian subject is a non-human mammal such as but not limited to a horse, cow, sheep, goat, pig, alpaca, llama, dog, cat or camel.

In an embodiment, the mammalian subject is in need of treatment. The term "treatment" encompasses the repair, regeneration or promotion of regeneration and/or reparation of cells, tissues and physiological pathways including neuronal and endocrinal pathways. Examples include but the present invention is not limited to, repair, regeneration and/or reparation of organs including, circulatory vessels, such as capillaries, arteries and veins including such vessels following ischemic-reperfusion injury or stroke, internal and surface wounds, ulcers and scars, neurodegenerative conditions and injury to the brain and spinal cord including traumatic brain injury and spinal cord injury. The exosomes are also proposed for the treatment of organ fibrosis such as fibrotic diseases, conditions or disorders of the lung, liver, heart, kidney and pancreas. The exosomes are also contemplated for use in the treatment of demyelination diseases, conditions or disorders or diseases such as multiple sclerosis, optic neuritis, Devic's disease, transverse myelitis, acute disseminated encephalomyelitis and adrenoleukodystrophy and adrenomyeloneuropathy. The amniotic exosomes are useful in clinical applications to treat a disease or condition as well as a cosmetic agent to promote skin regeneration or scar or wound healing.

Whilst not intending to limit the present invention to any one theory or mode of action, it is proposed herein that the mammalian amniotic exosomes represents a vesicular vehicle for communication from amnion epithelial cells and release proteomic and genetic molecules which provide a cocktail of beneficial molecules to facilitate repair, regeneration and reparation. It is also proposed that the profile of proteomic and genetic molecules will differ depending on the gestational stage of the donor from which the amnion epithelial cells are obtained. Hence, the present specification teaches the creation of a bank of immortalized mammalian amnion epithelial cells from different donors at different gestational stages. Epithelial cells are then selected from the bank based on the disease or condition in the subject to be treated and based on prolife of proteomic and genetic molecules the amniotic exosomes produce. The present specification teaches that depending on the disease or condition to be treated, amniotic exosomes having a particular proteomic and/or genetic prolife may be preferred.

Accordingly, another aspect taught herein is a method of treating a mammalian subject, the method comprising:
  i. optionally identifying a donor;
  ii. selecting immortalized amnion epithelial cells from the or a donor based on the proteomic and/or genetic profile of amniotic exosomes which are produced by the epithelial cells in culture;
  iii. generating conditioned medium from the selected immortalized amnion epithelial cells;
  iv. isolating amniotic exosomes from the conditioned medium; and
  v. systemically or locally administering the amniotic exosomes to the mammalian subject.

In an embodiment, the mammal subject is a human subject. Hence, another aspect taught herein is a method of treating a human subject, the method comprising:
  i. optionally identifying a donor;
  ii. selecting immortalized amnion epithelial cells from the or a donor based on the proteomic and/or genetic profile of amniotic exosomes which are produced by the epithelial cells in culture;
  iii. generating conditioned medium from the selected immortalized amnion epithelial cells;
  iv. isolating amniotic exosomes from the conditioned medium; and
  v. systemically or locally administering the amniotic exosomes to the human subject.

In another embodiment, mammalian amniotic exosomes are isolated and their proteomic and genetic profile predetermined and a bank of selected mammalian amniotic exosomes is generated based on the profiles. Particular amniotic exosomes are then selected for use in treatment.

Hence, the present specification is instructional for a method of treating a mammalian subject, the method comprising:
  i. optionally identifying a donor;
  ii. selecting amniotic exosomes from the or a donor based on the proteomic and/or genetic profile of agents released by the exosomes; and
  iii. systemically or locally administering the amniotic exosomes to the mammalian subject.

In an embodiment, the mammalian subject is a human.

Accordingly, taught herein is a method of treating a human subject, the method comprising:
  i. optionally identifying a donor;
  ii. selecting amniotic exosomes from the or a donor based on the proteomic and/or genetic profile of agents released by the exosomes; and
  iii. systemically or locally administering the amniotic exosomes to the human subject.

The amniotic exosomes when used in therapy may also be referred to as a medicament, agent, therapeutic, cell therapy derived agent, active ingredient and the like. Reference to "therapy" includes both clinical and cosmetic therapies.

Further taught herein is a method of inducing cellular or neuronal repair, regeneration and/or reparation in a mammalian subject, the method comprising the systemic or local administration to the mammalian subject of allogeneic amniotic exosomes for a time and under conditions sufficient to induce cellular or neuronal repair.

In an embodiment, a method in enabled herein of inducing cellular or neuronal repair, regeneration and/or reparation in a human subject, the method comprising the systemic or local administration to the human subject of allogeneic amniotic exosomes for a time and under conditions sufficient to induce cellular or neuronal repair.

In a further embodiment, contemplated herein is the use of mammalian amniotic exosomes in the manufacture of a medicament for cellular or neuronal repair, regeneration and/or reparation in a mammalian subject.

In an embodiment, the mammal is a human.

Hence, the present specification further teaches the use of human amniotic exosomes in the manufacture of a medicament for cellular or neuronal repair in a human subject. The present specification further teaches the use of human amniotic exosomes in the manufacture of a medicament for the treatment of a demyelinating disease, condition or disorder such as but not limited to multiple sclerosis.

Taught herein is an isolated sample of amniotic exosomes derived from amnion epithelial cell. This includes an isolated sample of human amniotic exosomes from human amniotic exosomes amnion epithelial cell. It is proposed to use these amniotic exosomes in an improved cell-based therapeutic protocol. The present invention extends, therefore, to a pharmaceutical composition comprising allogeneic mammalian amniotic exosomes selected for use to treat a mammalian subject, the pharmaceutical composition further comprising one or more pharmaceutically acceptable carriers, excipients and/or diluents.

In an embodiment, the mammalian subject is a human subject.

Hence, the present invention teaches a pharmaceutical composition comprising human allogeneic amniotic exosomes for use to treat a human subject, the pharmaceutical composition further comprising one or more pharmaceutically acceptable carriers, excipients and/or diluents.

In addition, the composition may be a cosmetic composition comprising human allogeneic amniotic exosomes for use to treat a human subject, the cosmetic composition further comprising one or more cosmetically acceptable carries, excipients and/or diluents.

Pharmaceutically acceptable carriers can contain a physiologically acceptable compound that acts to, for example, stabilize the amniotic exosomes. Physiologically acceptable compounds can include, for example, carbohydrates, such as glucose, sucrose, or a dextran, antioxidants, such as ascorbic acid or glutathione, chelating agents, low molecular weight proteins, or excipients including water or saline or other stabilizers and/or buffers. Detergents can also used to stabilize or to increase or decrease the absorption of the amniotic exosomes, including liposomal carriers. Pharmaceutically acceptable carriers and formulations are known to the skilled artisan and are described in detail in the scientific and patent literature, see e.g., Remington's Pharmaceutical Sciences (1990), 18$^{th}$ Edition, Mack Publishing Company, Easton, ("Remington's").

Other physiologically acceptable compounds include preservatives which are useful for preventing the growth or action of microorganisms in an amniotic exosome formulation. Various preservatives are well known and include, e.g., ascorbic acid. One skilled in the art would appreciate that the choice of a pharmaceutically acceptable carrier including a physiologically acceptable compound depends, for example, on the route of administration of the amniotic exosome of the present invention and on the particular physiological or biochemical of the proteins and nucleic acids produced by the exosomes.

Administration of the amniotic exosomes, in the form of a pharmaceutical composition, may be performed by any convenient means known to one skilled in the art and depending on the disease or condition or site of injury. Routes of administration include, but are not limited to, respiratorally, intratracheally, nasopharyngeally, intravenously, intraperitoneally, intrathoracically, subcutaneously, intracranially, intradermally, intramuscularly, intraoccularly, intrathecally, intracereberally, intranasally, rectally, topically, patch, bandage and implant. In an embodiment the amniotic exosomes can be sprayed onto, for example, subject with serious burn wounds.

The pharmaceutical forms suitable for injectable use include sterile aqueous solutions or dispersions.

Sterile injectable solutions in the form of dispersions are generally prepared by incorporating the various sterilized active ingredients into a sterile vehicle which contains the amniotic exosomes.

For parenteral administration, the amniotic exosomes may be formulated with a pharmaceutical carrier and administered as a suspension. Illustrative of suitable carriers are water, saline, dextrose solutions, fructose solutions, ethanol, or oils of animal, vegetative or synthetic origin. The carrier may also contain other ingredients, for example, preservatives, buffers and the like. When the amniotic exosomes are being administered intrathecally, they may also be formulated in cerebrospinal fluid.

For transmucosal or transdermal administration, penetrants appropriate to the barrier to be permeated can be used for delivering the agent. Such penetrants are generally known in the art e.g. for transmucosal administration, bile salts and fusidic acid derivatives. In addition, detergents can be used to facilitate permeation. Transmucosal administration can be through nasal sprays or using suppositories e.g, Sayani and Chien (1996) *Crit Rev Ther Drug Carrier Syst* 13:85-184.

The amniotic exosomes of the subject invention can also be administered in sustained delivery or sustained release mechanisms, which can deliver the exosomes internally over a period of time. For example, biodegradable microspheres or capsules or other biodegradable polymer configurations capable of sustained delivery of the amniotic exosomes can be included in the formulations of the invention (e.g., Putney and Burke (1998) *Nat Biotech* 16:153-157).

In preparing pharmaceutical compositions of the present invention, a variety of formulation techniques can be used and manipulated to alter biodistribution. A number of methods for altering biodistribution are known to one of ordinary skill in the art. Examples of such methods include protection of the exosomes in vesicles composed of substances such as proteins, lipids (for example, liposomes), carbohydrates, or synthetic polymers. For a general discussion of pharmacokinetics, see, e.g., Remington's.

The pharmaceutical compositions of the invention can be administered in a variety of unit dosage forms depending upon the method of administration. Such dosages are typically advisorial in nature and are adjusted depending on the particular therapeutic context. The amount of amniotic exosomes adequate to accomplish this is defined as the "effective amount". The dosage schedule and effective amounts for this use, i.e., the "dosing regimen" will depend upon a variety of factors, including the stage of the disease or condition, the severity of the disease or condition, the general state of the patient's health, the patient's physical status, age, pharmaceutical formulation and concentration or selective of amniotic exosomes. In calculating the dosage regimen for a patient, the mode of administration also is taken into consideration. The dosage regimen must also take into consideration the pharmaceutical composition's rate of clearance, and the like. See, e.g., Remington's; Egleton and Davis (1997), *Peptides* 18:1431-1439; Langer (1990), *Science* 249:1527-1533. In an embodiment, from point 0.05 µg to 100 µg of an amniotic exosomes are administered. In this includes from 0.1 µg to 50 µg and 0.1 µg to 20 µg and any amount in between.

In accordance with these methods, the amniotic exosomes or pharmaceutical compositions comprising same may be co-administered in combination with one or more other agents. Reference herein to "co-administered" means simultaneous administration in the same formulation or in two different formulations via the same or different routes or sequential administration by the same or different routes. Reference herein to "sequential" administration is meant a time difference of from seconds, minutes, hours or days between the administration of the amniotic exosomes and another agent. Co-administration may occur in any order. Examples of agents which could be co-administered include cytokines. Generally, the selection of another agent is predicated on the disease or condition to be treated.

Alternatively, targeting therapies may be used to deliver the amniotic exosomes to types of cells or locations in the body, by the use of targeting systems such as antibodies or cell specific ligands. Targeting may be desirable for a variety of reasons, e.g., to promote local treatment at a site in need of treatment.

Further taught herein is the production of amniotic exosomes. Conveniently, this is accomplished in a bioreactor which may be in the form of a batch culture reactor or a continuous flow culture reactor. Generally, the amnion epithelial cells are immortalized and are used to seed growth medium in the bioreactor. The resulting conditioned medium is then collected and the amniotic exosomes isolated and formulated for immediate use or stored such as by lyophilization for later use.

Kits are also contemplated herein. The kits may be therapeutic or diagnostic. The therapeutic kit may comprise a selected batch of lyophilized amniotic exosomes and one or more other pharmaceutically acceptable carriers, excipients and/or diluents and/or another active agent. A diagnostic kit may comprise reagents to determine the proteomic or genetic profile of a batch of amniotic exosomes.

EXAMPLES

Aspects taught herein are now further described by the following non-limiting Examples.

Example 1

Production of Amniotic Exosomes

Figure 1:
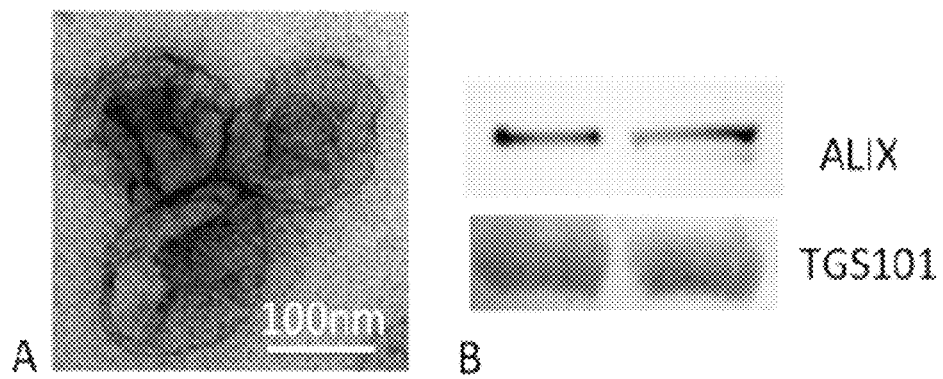
FIG. 1 is a photographic representation of (A) an electron micrograph of amniotic exosomes showing typical cup-shaped morphology and approximately 100 nm diameter; (B) expression of markers of exosome biogenesis, Alix and TSG101. Alix and TSG101 are exosome biomarkers.

A protocol is developed to isolate amniotic exosomes (FIG. 1). This is the first description of amniotic exosomes and verification of their biological activity. Primary isolates of hAECs are cultured in serum-free media (Ultraculture media, Lonza) for 96 hours before the cells are removed and conditioned media processed for exosome isolation via serial ultracentrifugation at 110,000 g. Approximately 1.5-2 µg purified exosomes per million hAECs are consistently purified regardless of gestational age. This can be scaled up in bioreactor-style cultures without contamination by apoptotic bodies.

Figure 2:
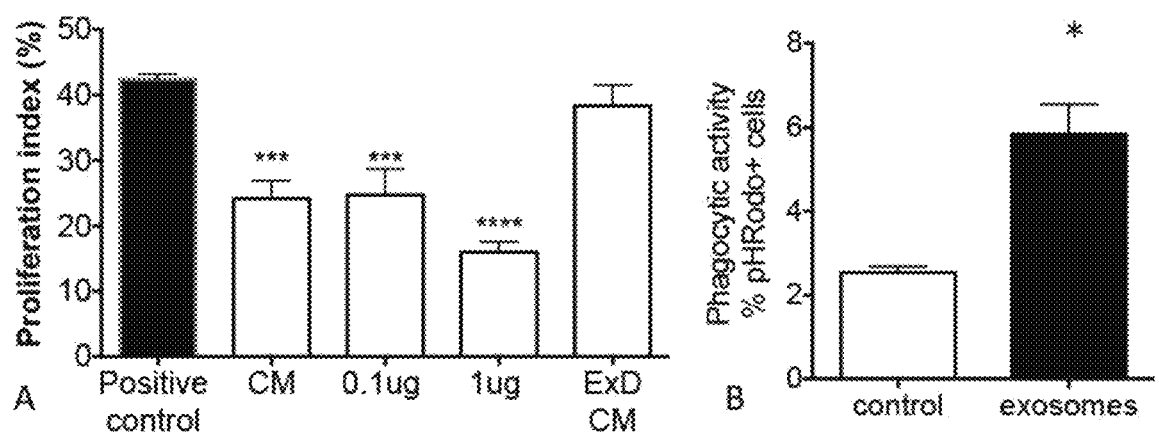
FIG. 2 is a graphical representation showing that (A) amniotic exosomes inhibit T-cell proliferation similarly to hAEC conditioned media; (B) amniotic exosomes increase macrophage phagocytosis n=3.

The ability of the amniotic exosomes to exert a similar effect was tested. Amniotic exosomes suppress T cell proliferation to a similar extent as hAEC conditioned media, with apparent dose effect (0.1 µg vs 1 µg). Depletion of exosomes from hAEC conditioned media (ExD CM) abolished this effect (FIG. 2A), indicating that amniotic exosomes are a major mediator of T cell suppression. Amniotic exosomes were able to directly increase phagocytic activity of macrophages (FIG. 2B). These findings indicate that the immunomodulatory effects of hAEC conditioned media are largely attributed to exosomes.

Example 2

Activity of Amniotic Exosomes

Figure 3:
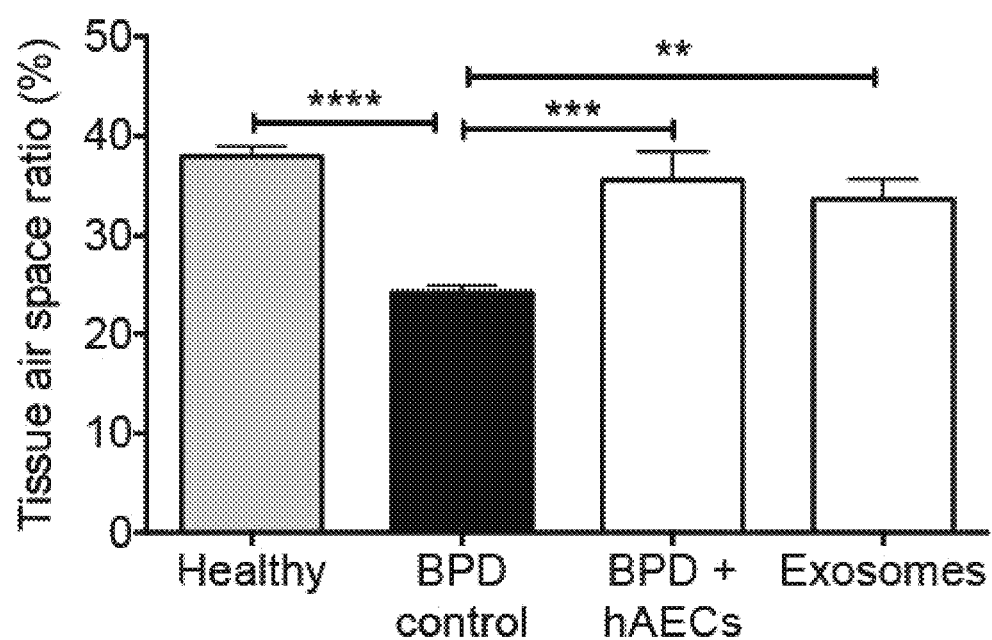
FIG. 3 is a graphical representation showing the tissue: airspace ratio is improved by amniotic exosomes in a bronchopulmonary dysplasia (BPD) mouse model.

It was determined whether amniotic exosomes were functional in vivo. An aliquot of 1 µg of amniotic exosomes were injected intravenously to BPD mice at postnatal day 4 and an assessment of tissue:airspace ratio performed at postnatal day 14. Amniotic exosomes were effective in reversing alveolar simplification (FIG. 3). Amniotic exosomes play a major role by which they prevent or reverse detrimental changes to lung architecture—by reducing alveolar simplification and recruiting endogenous stem cells, while resolving inflammation in BPD mice.

In summary, the data indicate that amniotic exosomes modulate host immunological events and lung repair in a manner similar to their parent cells. It is proposed that amniotic exosomes can recapitulate the regenerative capabilities of hAECs in vivo. By uncovering the nature of the amniotic exosomal cargo, they can be used to exert a profound immunomodulatory and pro-reparative effect.

A mouse model of BPD is used to determine that neonatal administration of amniotic exosomes can recover lung structure, activate lung stem cell niches and modulate inflammation in BPD mice to levels comparable to that of hAEC treated animals. It is further determined that this will result in improvements in long term physiological outcomes (e.g., pulmonary hypertension and lung function). Proteomic and mRNA/miRNA content of amniotic exosomes are analyzed to identify specific pathways associated with hAEC-mediated repair.

Example 3

Reparative Effects of Amniotic Exosomes in BPD Mice

Data indicate that amniotic exosomes exert immunomodulatory and proregenerative effects in vitro and in vivo. To understand how amniotic exosomes affect cellular crosstalk during repair and determined whether amniotic exosomes alone are sufficient to recapitulate the reparative effects of hAECs in an animal model of BPD, the effects of two doses of amniotic exosomes (1 µg and 10 µg) are compared against an optimized dose of hAECs. Fibroblasts and fibroblast exosomes are used as controls.

Figure 4:
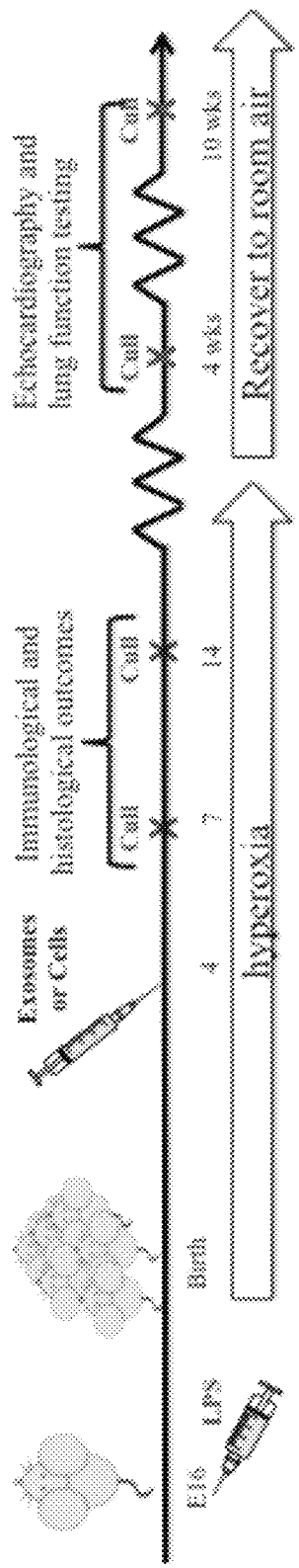
FIG. 4 is a diagrammatic representation of the experimental time used in Example 3 depicting intra-amniotic LPS injection at E16, injection of exosomes/cells at postnatal day 4 and cull points (crosses).

A mouse model of BPD is used, which combines two major contributing factors to human BPD—perinatal inflammation and postnatal hyperoxia—to assess the effects of term and preterm amniotic exosomes on lung repair. While there are limitations to modelling a complex disease like BPD using rodents, this model lends itself to detailed molecular analysis. Rodent studies allow relative affordability for the assessment of dose effects, and long term studies looking into adolescent and adult outcomes. Briefly, 0.2 g lipopolysaccharide (LPS) in 5 µL saline is injected into each amniotic sac of mouse fetuses at E16 using microforged glass needles (internal diameter: 70-80 µm) and a microinjector (IM-300, Narashige). Once born, newborn mouse pups and their nursing dams are placed into either a hyperoxia chamber (65% oxygen) or room air. Nursing dams are rotated every 48 hours to prevent oxygen toxicity. This combination of prenatal inflammation and postnatal hyperoxia causes lung injury resembling human BPD (Vosdoganes et al. (2013) *Cytotherapy* 15:1021-1029; Nold et al. *Proc. Natl Acad. Sci USA* 110:14384-14389) Therapy is administered on postnatal day 4. The experimental timeline depicting intra-amniotic LPS injection at E16, injections of exosomes/cells at postnatal day 4 and cull points (crosses) is shown in FIG. 4.

Exosomes or cells are administered intravenously through the superficial temporal vein, using the same equipment described for intra-amniotic injections and wider glass needles (100-120 µm internal diameter). The final injection volume is 10 µL, which is well tolerated by 4-day old mice. Mouse pups are culled at postnatal days 7 and 14 for assessment of immunological changes and lung stem cell recruitment and lung repair. Two cohorts of animals are then transferred into room air after weaning and tested at 4- and 10-weeks of age to assess the effects of neonatal therapy on long term outcomes, e.g., pulmonary hypertension, cardiovascular and respiratory function during adolescence and early adulthood.

hAECs are isolated from term (37-40 weeks) human pregnancies. Primary isolates are used for the experiments. hAECs from six donors are equally pooled to provide a uniform population for all animal experiments. Animals receiving hAECs receive a single injection of 100,000 hAECs on postnatal day 4. For amniotic exosomes, a portion of the pooled hAECs is placed into culture media (10 million per 25 mL Ultraculture media, Lonza) for 96 hours. Exosomes are then isolated from the conditioned media. The exosomal nature of the isolated pellet by performing western blots for exosomal markers (TSG101 and Alix) as well as size and discrimination by electron microscopy. Exosomes are resuspended in saline and administered at a dose of either in 1 µg or 10 µg at postnatal day 4.

Human lung fibroblasts do not support lung repair and are suitability as a control cell type (Moodley et al. (2010) *Am*

*J Respir Crit Care Med* i:643-651). Human lung fibroblasts or fibroblast exosomes obtained using the same culture protocol as above are administered. Fibroblasts are administered at the same dosage as hAECs and fibroblast exosomes at the higher dosage (10 μg). Experimental groups are described in the Table 1.

TABLE 1

Experimental Groups

| Healthy mice | | Group | BPD mice | | Group |
|---|---|---|---|---|---|
| Saline | — | 1 | Saline | — | 7 |
| hAECs | 100,000 cells | 2 | hAECs | 100,000 ells | 8 |
| Amniotic exosomes | 1 μg | 3 | Amniotic exosomes | 1 μg | 9 |
| | 10 μg | 4 | | 10 μg | 10 |
| Fibroblasts | 100,000 ells | 5 | Fibroblasts | 100,000 cells | 11 |
| Fibroblast exosomes | 10 μg | 6 | Fibroblast exosomes | 10 μg | 12 |

Immunological Changes

Lungs are collected and processed for flow cytometry as previously described (Nold et al. (2013) supra; Tan et al. (2015) *Stem Cell Res. Ther.* 6:8). The CD45+fraction is sorted and a combination of surface markers and intracellular cytokine stains used to assess changes to numbers, phenotypes and activation states of T-cells (CD3, CD4, CD25, IFNγ, IL-4, IL17A, FoxP3), macrophages (CD11b, F4/80, CD86, MHCII), neutrophils (CD11c, Ly6G), B cells (B220) and NK cells (NK1.1). Bronchoalveolar lavage fluid is collected to measure changes in cytokines using a Proteome Profiler (R&D Systems) as previously described (Nold et al. (2013) supra).

Lung Stem/Progenitor Cell Recruitment

Changes to the BASC population are determined by flow sorting based on the criteria CD45−/CD31−/Sca-1+/Ep-Cam+ (Lee et al. (2014) *Cell* 156: 440-455). This uses the CD45+ fraction of cells from the immune cell study above. AT2 is sorted based on flow sorting of CD31−/Sca-1−/autofluorescent$^{high}$. Differences in transcriptional profiles is determined using single cell digital PCR (Fluidigm, qdPCR 37K). Flow sorted single cells are captured on a 96-well microfluidic plate (C1 Single Cell Autoprep System, Fluidigm) where cell lysis, RNA isolation, pre-amplification and cDNA conversion will occur. The samples are then loaded onto microfluidic cards for digital PCR. Data are analyzed using the SINGuLAR v2.0 analysis toolset. Since niche activation pathways of BASC and AT2 are poorly described, a customized 48:48 deltaGene assay that covers stem cell pluripotency, activation, recruitment and differentiation, including the recently described BMP1/NFATc1/Thrombospondin-1 axis (Lee et al. (2014) supra).

Alveolar Simplification

Quantitative image analysis measuring tissue:airspace ratio is preformed to determine the extent of alveolar simplification across all experimental groups.

Activation of Host Stem Cell Niche

Immunohistochemical staining (SPC+CC10+) is performed for BASCs at the terminal bronchioles to determine activation states of lung stem cell niches (Lee et al. (2014) supra).

The aim is to know if changes to lung structure and recruitment of endogenous lung stem cells extend to long term improvements in lung function and reduced secondary complications.

Physiological Studies

Lung function testing and echocardiography is performed on recovered adolescent (4-week old) and young adult (10-week old) mice.

Echocardiography

The mice are anaesthetized with 3% isoflurane and continued at 1-2% to achieve a heart rate of 350-450 bpm. The Vevo 2100 ultrasound (Monash Bioimaging) and a 40 MHz linear transducer are used to perform PW doppler measurements of pulmonary artery acceleration time along the anteriorly angulated left parastemal long axis view. Right ventricular wall thickness is measured by applying the M mode along the right parasternal long axis view. The same groups of mice are used for invasive lung function testing. They are tracheostomized with an 18G cannula connected to an inline ultrasonic nebuliser, ventilator and attached pressure transducer (FlexiVent, SCIREQ, Montreal, Canada). Airway resistance and compliance are assessed by exposing the mice to increasing concentrations of methacholine (1-30 mg/mL, 3 mins per cycle). Forced expired volumes, vital capacity and inspiratory capacity are obtained. Unlike unrestrained whole body plethysmography, this does not require training of animals and enables a brief pause in mechanical ventilation to execute measurement maneuvers during which predefined pressures or volume waveforms are measured. This overcomes traditional challenges faced in plethysmography such as excessive dead space and measurement inaccuracies.

It is proposed that amniotic exosomes will have a beneficial effect in their ability to trigger macrophage polarization, induce Treg expansion, and reduce activation of neutrophils and dendritic cells in BPD mice. Immunological changes are proposed to be more profound with the 10 μg dose of amniotic exosomes compared to 1 μg of control hAECS. As such, reversal of alveolar simplification is greater in the animals that receive the higher dose of amniotic exosomes. This translates to improvements in long term physiological outcomes such that there will be dose-dependent reduction in right ventricular wall thickening, amelioration of pulmonary hypertension and restoration of normal lung function. No changes are expected when hAECs or amniotic exosomes are given to healthy mice. Fibroblasts or fibroblast exosomes are not proposed to have an effect on immune cells, lung repair or long term physiological outcomes.

Example 4

Unique Mediators in Amniotic Exosomes

The gestational age of the hAEC donor can have significant impact on their reparative capacity (Lim et al. (2013) *Placenta* 34: 486-492). A comparison is made between exosomal cargo collected from term and preterm hAECs. In preparation, amniotic exosomes from term and preterm donors are administered and showed that alveolar simplification is only reversed in animals that received the amniotic exosomes from term donors, thus indicating that the ability to activate pathways for immune modulation and regeneration are significantly impaired in preterm amniotic exosomes. When an initial presence/absence proteomic analysis is performed on the exosomal cargo, 242 and 21 unique proteins in the term and preterm donor, respectively are identified. Using gene ontology analysis, it is determined that term amniotic exosomes contained mediators of cell signaling associated with wound healing, apoptosis, vascular development, acute inflammation and epithelial cell development.

For proteomic analysis, an in-solution trypsin digest of amniotic exosomes (term and preterm, n=10 per group) is performed followed by liquid chromatography and mass spectrometry for absolute quantitation (WEHI Proteomics Laboratory, Melbourne, Australia). Data are acquired using a Q-Exactive hybrid quadrupole-orbitrap mass spectrometer fitted to a Nano-ESI source (Proxeon) coupled to a nano-ACQUITY UPLC system (Waters). Peak lists are merged for each LC-MS/MS run into a single MASCOT file and search against a human Ref-Seq protein database (1% false discovery rate). Pipeline Pilot (Accelrys) and Spotfire (TIBCO) is used to analyze quantitative proteomics data. Wilcoxon signed-rank test is used to evaluate differences in abundance. The UniProt database issued to classify proteins based on function, subcellular localization, and specify genes involved in wound healing, cell survival and immune modulation.

For nucleic acid analysis, digital gene expression profiling is performed using Massive Analysis of cDNA ends (MACE, GenXpro GmbH). This allows the capture and quantification rare of transcripts at ~20 times deeper than RNASeq (1-20 copies per million transcripts) such as receptors and transcription factors, which are usually lost in microarrays. MACE is optimized to sequence small RNA and miRNA from exosomes and combines the benefits of qPCR arrays and RNASeq by tagging each cDNA molecule. It identifies alternative polyadenylation, which influences mRNA-miRNA interaction and thus determines stability and biological relevance of transcripts. Gene ontology enrichment and gene set enrichment analysis for pairwise comparisons are preformed.

There will be unique molecular signatures between term and preterm amniotic exosomes, which relate to their pro-reparative and regenerative effects.

Example 5

Pro-Regenerative Effects

The pro-regenerative effects of amniotic exosomes was demonstrated in a neonatal mouse model of bronchopulmonary dysplasia. Alveolar pruning was observed following the administration of exosomes from term or preterm amniotic tissue (FIGS. 12A through D). The term "BPD" means the bronchopulmonary dysplasia mouse model animals.

Example 6

Mechanism of Action of Exosomes

Figure 13:
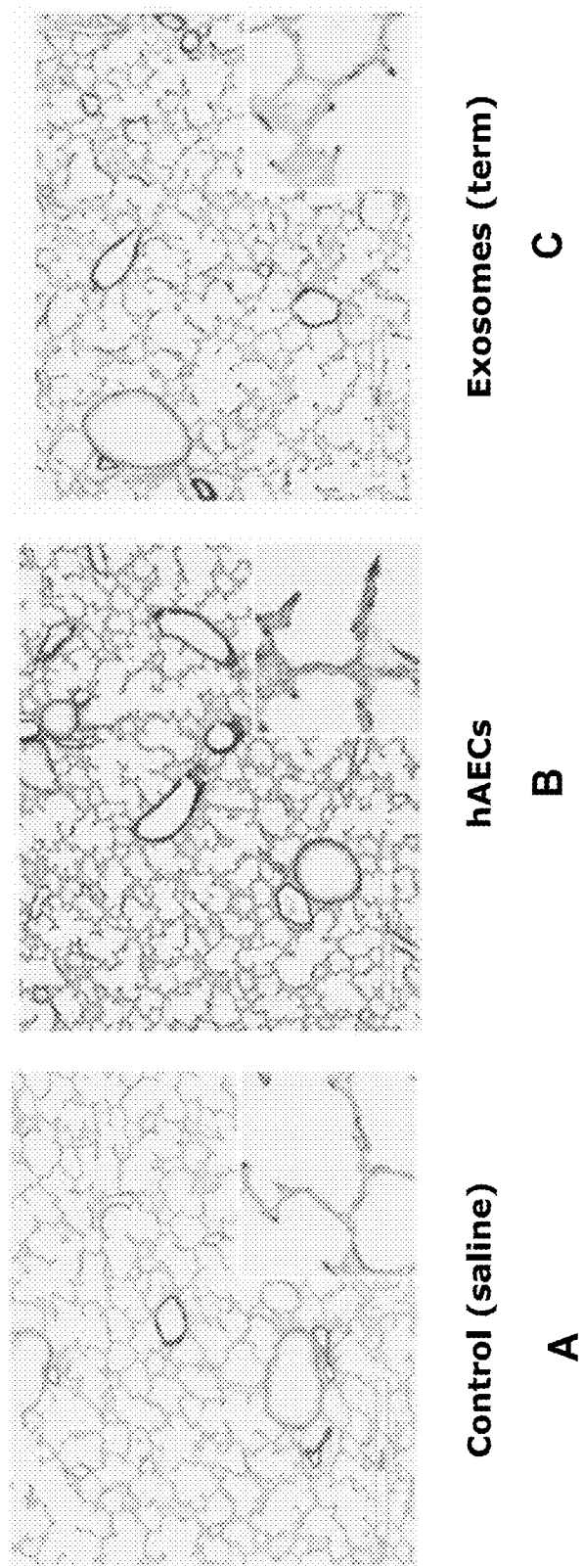
FIG. 13A through C are photographic representations showing that amniotic exosomes trigger regeneration in the lungs as do hAECs. The dark stain is evidence of elastin-positive tips.

Term-derived human exosomes were tested along side human amniotic epithelial cells (hAECs) for ability to induce lung regeneration. The results are shown in FIGS. 13A through C. Term exosomes restored secondary septal crests as seen as dark stained (elastin positive) tips in FIG. 13.

Figure 14:
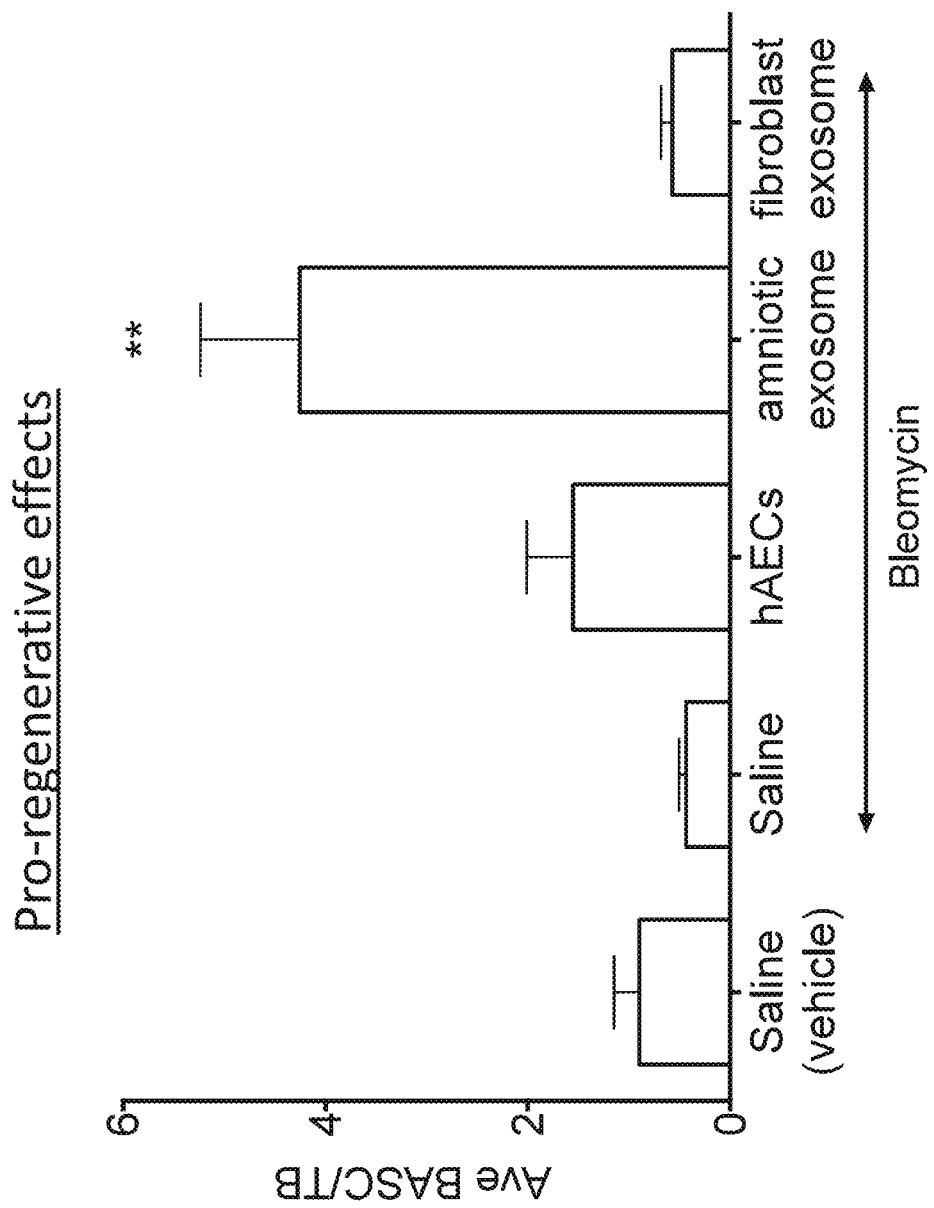
FIG. 14 is a graphical representation showing that amniotic exosomes, but not fibroblast exosomes, trigger an endogenous stem cell response in the lungs. This response is significantly greater than the response induced by hAECs.

In addition, FIG. 14 shows that amniotic exosomes trigger an endogenous stem cell response in the lungs. In fact, amniotic exosomes were more than twice as effective as were hAECs.

Also observed was that amniotic exosomes could directly stimulate enhancement in the growth of exogenous lung stem cells. This occurred in alveolar, bronchiolar and mixed lung tissue exposed to exosomes, relative to a control.

Example 7

Exosomes are Anti-Fibrotic in Liver

Figure 15:
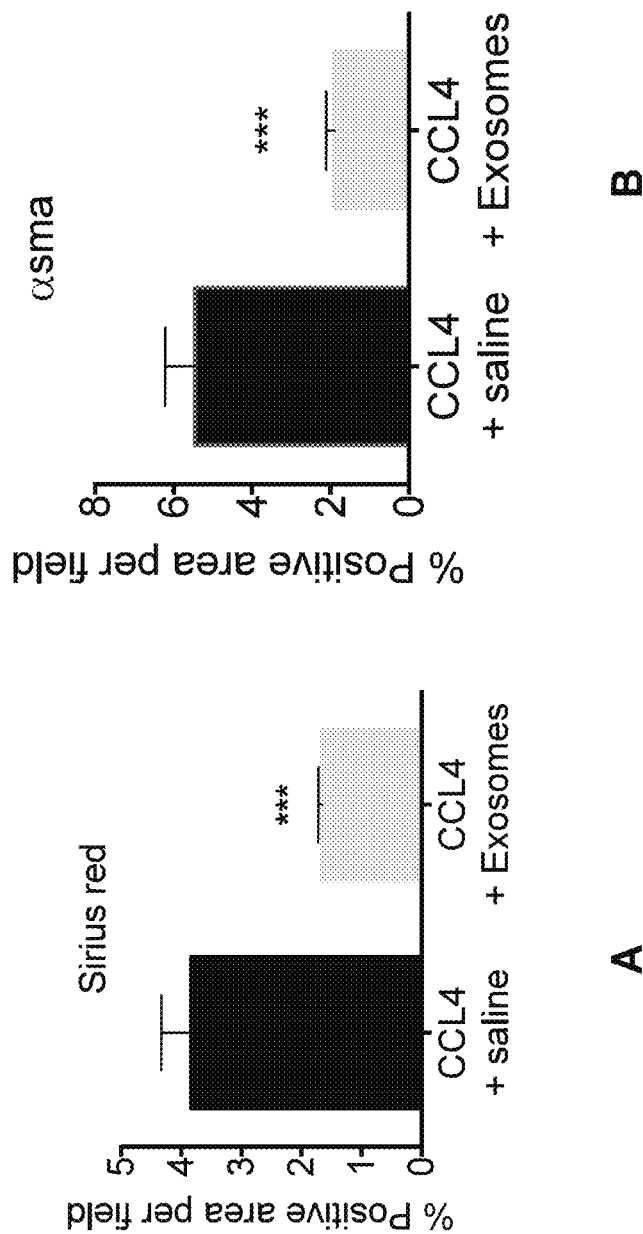
FIGS. 15A and B show that amniotic exosomes were anti-fibrotic in the liver as evidenced using the Sirius red stain (A) and α-smooth muscle activin (α-SMA) immunohistochemical analysis of histological liver sections CCL4+saline versus CCL4+exosome.

Liver fibrosis was induced in adult mice aged 8-12 weeks by 3× weekly intraperitoneal injection of carbon tetrachloride for 12 weeks. At week 8, exosomes (1 g) were twice weekly injected. The results are shown in FIGS. 15A and B. Fibrobiotic cells were determined using the Sirius red assay and the α-smooth muscle action (SMA) expression assay. α-SMA plays a role in fibroblast contractility. α-SMA expression was determined using standard assays and Sirius red or α-SMA positive areas were measured per field. The inflammatory macrophage protein, CCL14, was used. CCL14+exosomes resulted in significant less fibrotic cells per field compared to CCL14+saline control (FIGS. 15A and B).

Example 8

Proteomic Cargo

Figure 16:
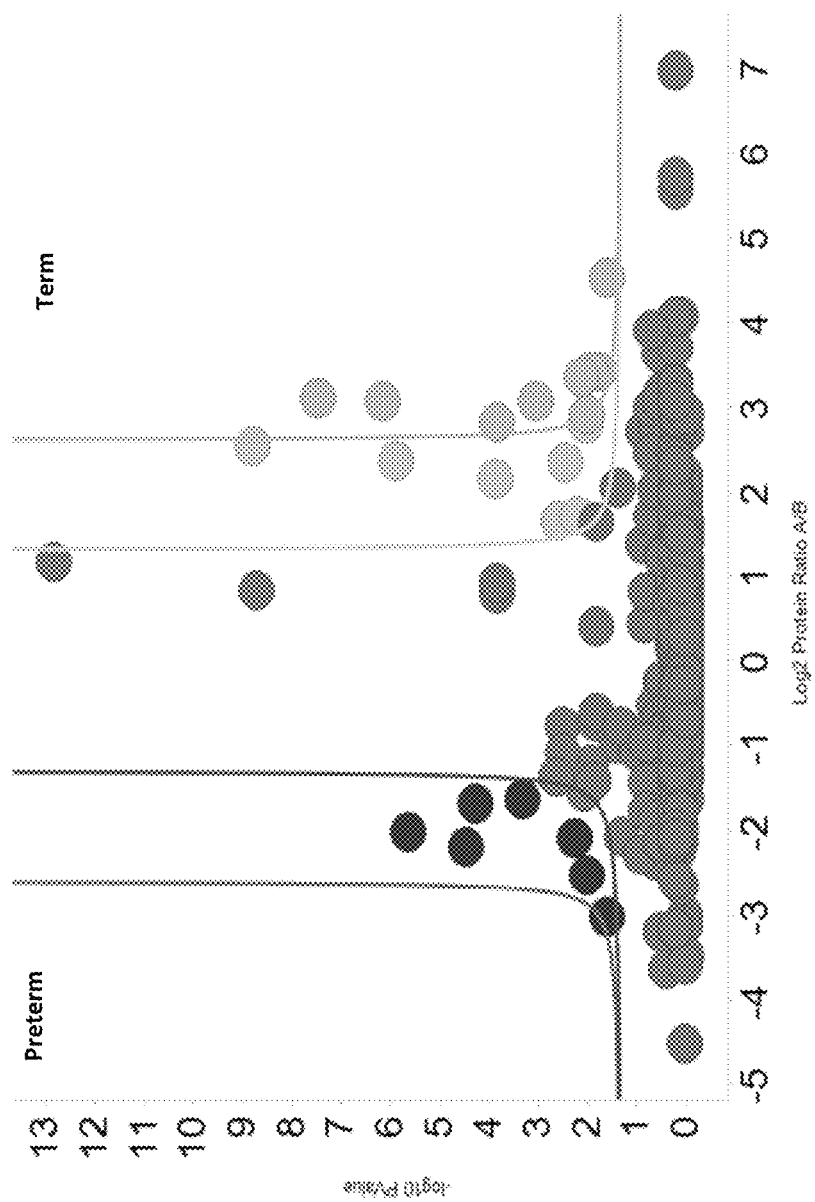
FIG. 16 is a graphical representation showing the differences at the proteomic level between exosomes from term versus preterm hAECs.
Figure 17:
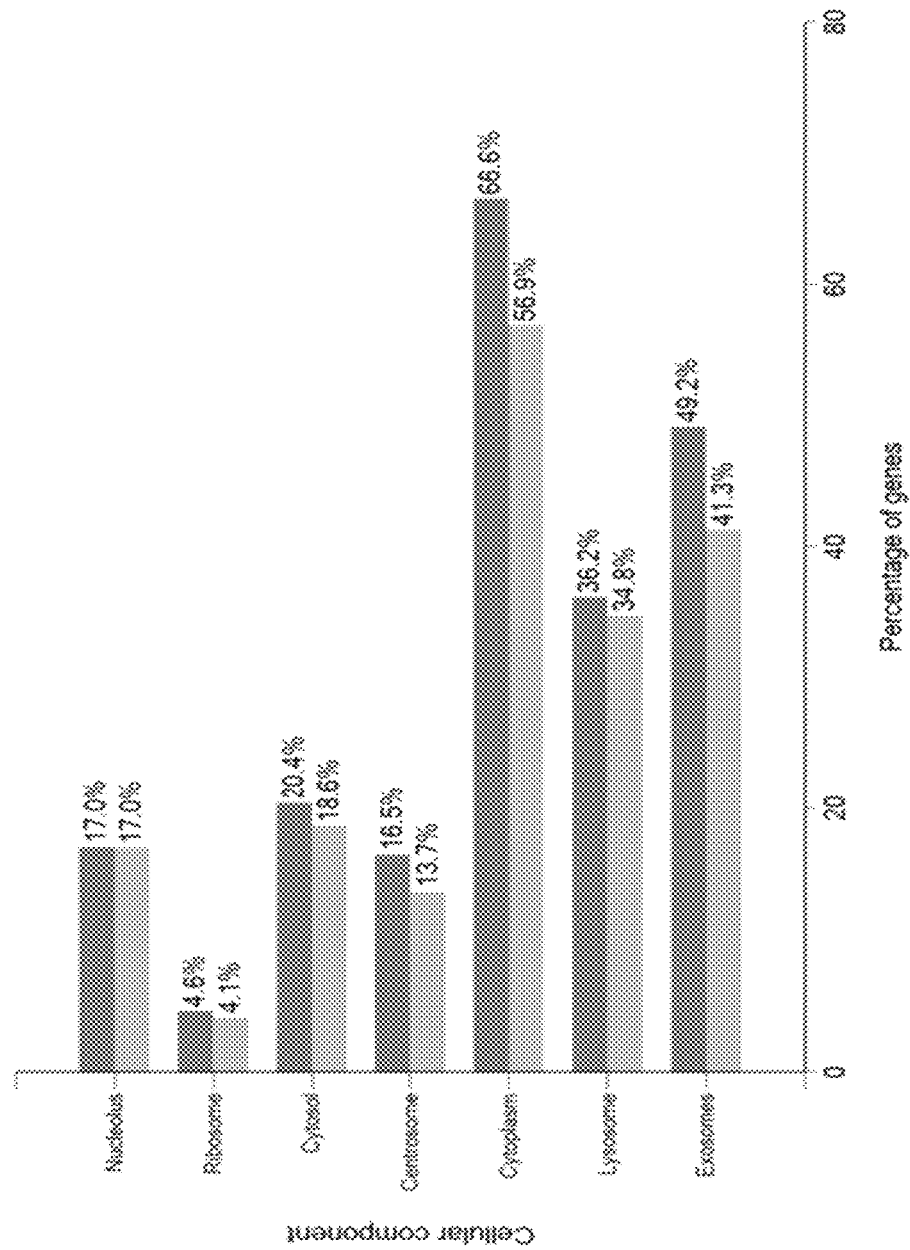
FIG. 17 is a graphical representation of a cellular component comparison between hAECs and total mesenchymal stem cells (MSCs).

FIG. 16 shows that the proteomic cargo between term exosomes and preterm hAECs is about the same. There was more of a difference between the proteomic cargo of term versus preterm hAECs. Proteins tested are listed in Tables 2a and 2b. A useful cellular component comparison is shown in FIG. 17 between hAEC and total MSC. FIG. 18 also compares biological processes between hAECs and total MSC.

TABLE 2a

Proteomic cargo in amniotic exosomes: Proteins common to MSCs

| Search ID/ Accessions | Gene Symbol | Entrez Gene ID | Gene Description |
|---|---|---|---|
| PGK2 | PGK2 | 5232 | phosphoglycerate kinase 2 |
| CAND2 | CAND2 | 23066 | cullin-associated and neddylation-dissociated 2 (putative) |
| CCDC80 | CCDC80 | 151887 | coiled-coil domain containing 80 |
| RAB12 | RAB12 | 201475 | RAB12, member RAS oncogene family |
| RAD23B | RAD23B | 5887 | RAD23 homolog B (S. cerevisiae) |
| DBN1 | DBN1 | 1627 | drebrin 1 |
| STRAP | STRAP | 11171 | serine/threonine kinase receptor associated protein |
| UBA6 | UBA6 | 55236 | ubiquitin-like modifier activating enzyme 6 |
| PEA15 | PEA15 | 8682 | phosphoprotein enriched in astrocytes 15 |
| GLOD4 | GLOD4 | 51031 | glyoxalase domain containing 4 |
| COPE | COPE | 11316 | coatomer protein complex, subunit epsilon |
| BCAT1 | BCAT1 | 586 | branched chain amino-acid transaminase 1, cytosolic |
| FSTL1 | FSTL1 | 11167 | follistatin-like 1 |
| DYNC1LI2 | DYNC1LI2 | 1783 | dynein, cytoplasmic 1, light intermediate chain 2 |
| GPS1 | GPS1 | 2873 | G protein pathway suppressor 1 |
| SPATA5 | SPATA5 | 166378 | spermatogenesis associated 5 |
| COPS5 | COPS5 | 10987 | COP9 signalosome subunit 5 |
| GYG1 | GYG1 | 2992 | glycogenin 1 |
| TCEB2 | TCEB2 | 6923 | transcription elongation factor B (SIII), polypeptide 2 (18 kDa, elongin B) |
| APOC2 | APOC2 | 344 | apolipoprotein C-II |
| MAPK3 | MAPK3 | 5595 | mitogen-activated protein kinase 3 |
| RUFY1 | RUFY1 | 80230 | RUN and FYVE domain containing 1 |

TABLE 2a-continued

Proteomic cargo in amniotic exosomes: Proteins common to MSCs

| Search ID/ Accessions | Gene Symbol | Entrez Gene ID | Gene Description |
|---|---|---|---|
| HDLBP | HDLBP | 3069 | high density lipoprotein binding protein |
| TTC37 | TTC37 | 9652 | tetratricopeptide repeat domain 37 |
| UBA2 | UBA2 | 10054 | ubiquitin-like modifier activating enzyme 2 |
| NCS1 | NCS1 | 23413 | neuronal calcium sensor 1 |
| CAV2 | CAV2 | 858 | caveolin 2 |
| TM9SF4 | TM9SF4 | 9777 | transmembrane 9 superfamily protein member 4 |
| EIF5B | EIF5B | 9669 | eukaryotic translation initiation factor 5B |
| TXNL1 | TXNL1 | 9352 | thioredoxin-like 1 |

TABLE 2b

Proteomic cargo in amniotic exosomes: Proteins unique to hACEs

| Search ID/ Accessions | Gene Symbol | Entrez Gene ID | Gene Description |
|---|---|---|---|
| TNXA | | | |
| TES | TES | 26136 | testis derived transcript (3 LIM domains) |
| NPEPPSL1 | | | |
| UPK3BL | | | |
| POLR2J3 | | | |
| DKFZp586I031 | | | |
| SEPT14 | SEPT14 | 346288 | septin 14 |
| DKFZp313C1541 | | | |
| SLC2A14 | SLC2A14 | 144195 | solute carrier family 2 (facilitated glucose transporter), member 14 |
| PPIAL4C | | | |
| PPIAL4E | | | |
| PPIAL4D | PPIAL4D | 645142 | peptidylprolyl isomerase A (cyclophilin A)-like 4D |
| CRABP1 | CRABP1 | 1381 | cellular retinoic acid binding protein 1 |
| Sep-02 | | | |
| TPPP3 | TPPP3 | 51673 | tubulin polymerization-promoting protein family member 3 |
| Sep-08 | | | |
| ARPC4-TTLL3 | | | |
| KIF5C | KIF5C | 3800 | kinesin family member 5C |
| KIF5A | KIF5A | 3798 | kinesin family member 5A |
| NSFL1C | NSFL1C | 55968 | NSFL1 (p97) cofactor (p47) |
| PERP | PERP | 64065 | PERP, TP53 apoptosis effector |
| SKP1 | SKP1 | 6500 | S-phase kinase-associated protein 1 |
| ALPPL2 | ALPPL2 | 251 | alkaline phosphatase, placental-like 2 |
| ALPI | ALPI | 248 | alkaline phosphatase, intestinal |
| PCYT2 | PCYT2 | 5833 | phosphate cytidylyltransferase 2, ethanolamine |
| CDH3 | CDH3 | 1001 | cadherin 3, type 1, P-cadherin (placental) |

Example 9

Exosomes Promote Myelination

Amniotic exosomes are tested in animal models of multiple sclerosis. It is expected that the exosomes will promote remyelination and be useful in the treatment of multiple sclerosis as well as other conditions such as optic neuritis, Devic's disease, transverse myelitis, acute disseminated encephalomyelitis and adrenoleukodystrophy and adrenomyeloneuropathy.

Example 10

Exosome Activity

Exosome isolated from the conditioned media of human amnion epithelial cells have immunomodulatory and pro-regenerative effects. The amniotic exosomes contain (amongst) other factors), high level of HLA-G.

Immunosuppressive effectives of amniotic exosomes correspond to the gestational age of the donor. This corresponds to donor potency associated with gestational age, which we have previously published in (Lim et al. (2013) supra).

Figure 5:
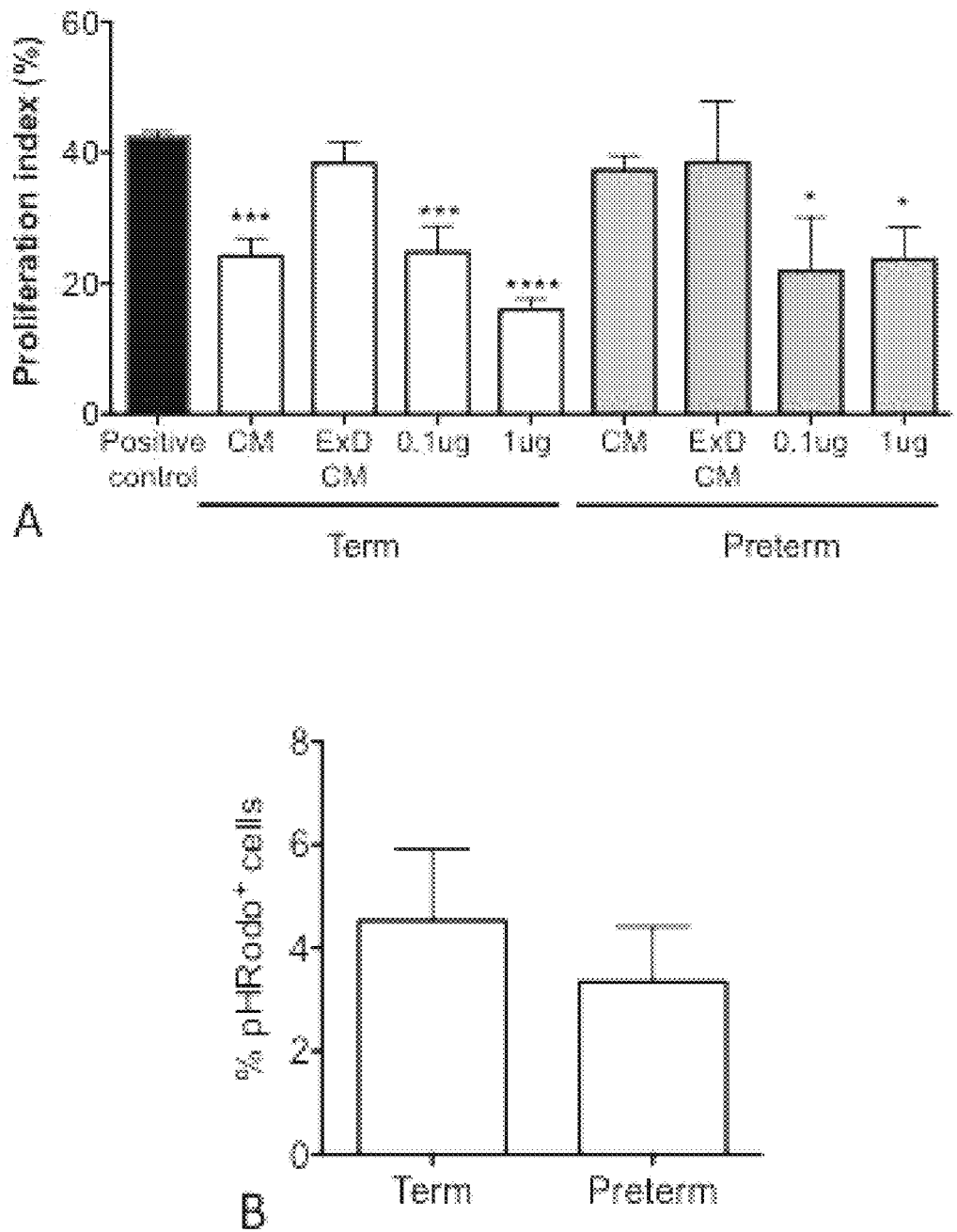
FIG. 5 is a graphical representation showing that (A) term exosomes are more immunosuppressive than preterm exosomes; (B) term exosomes are better able to increase macrophage phagocytosis as shown by pHRodo labelling n=3 donors per group.

Amniotic exosomes reverse lung injury in a neonatal mouse model of bronchopulmonary dysplasia. Intravenously injected exosomes significantly improve tissue:airspace ratio compared to saline, and consistent to our in vitro, term amniotic exosomes were superior to preterm exosomes in their ability to mitigate BPD related lung damage. This is associated with an activation of the endogenous stem cell niche of the lungs i.e. bronchioalveolar duct junction. The results are shown in FIG. 5. It is proposed that the amniotic exosomes will be useful in the treatment of lung fibrosis and fibrosis of other organs.

Figure 6:
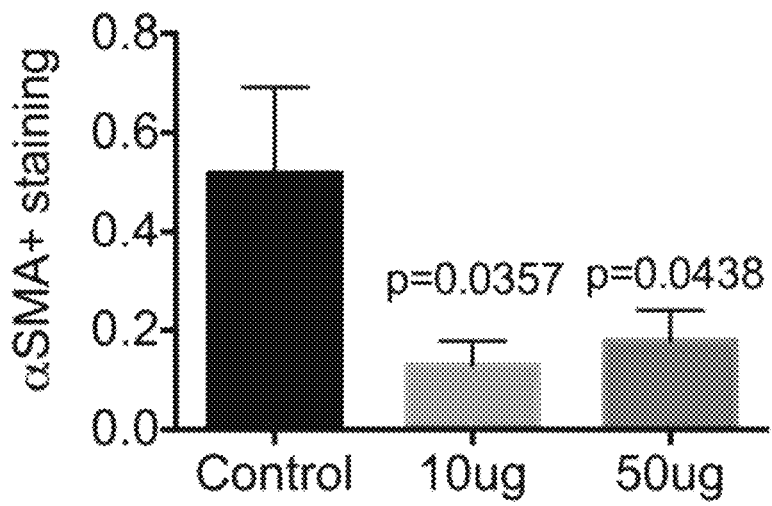
FIG. 6 is a graphical representation showing that amniotic exosomes reverse established lung inflammation and fibrosis in a mouse model of bleomycin-induced lung fibrosis. (A); (B) 6-8 month old female C57Bl6 mice. 10 µg or 50 µg exosomes from term hAECs, administered intranasally 7 days following bleomycin challenge.
Figure 6:
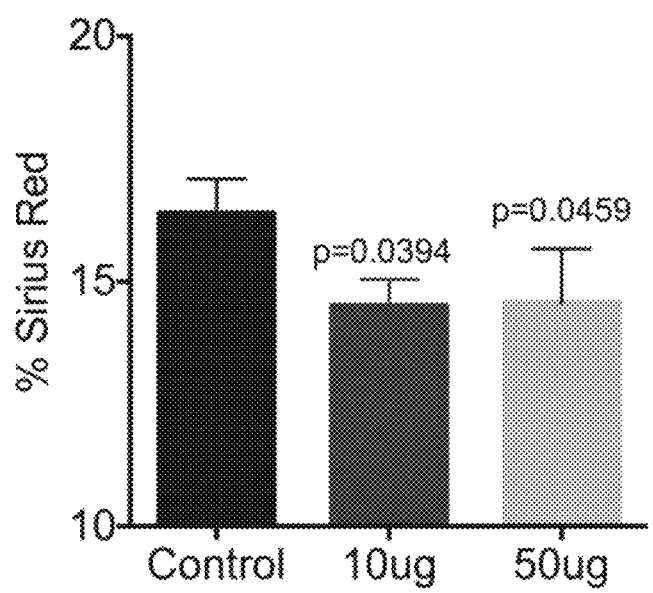

Amniotic exosomes reverse established lung inflammation and fibrosis in a mouse model of bleomycin induced lung fibrosis. Intranasal administration of amniotic exosomes 7 days post bleomycin challenged significantly reduced the percentage of activated myofibroblasts (α-smooth muscle actin positive) in the lungs. This was consistent with the reduction in collagen deposition in the lungs. The results are shown in FIG. 6.

Figure 7:
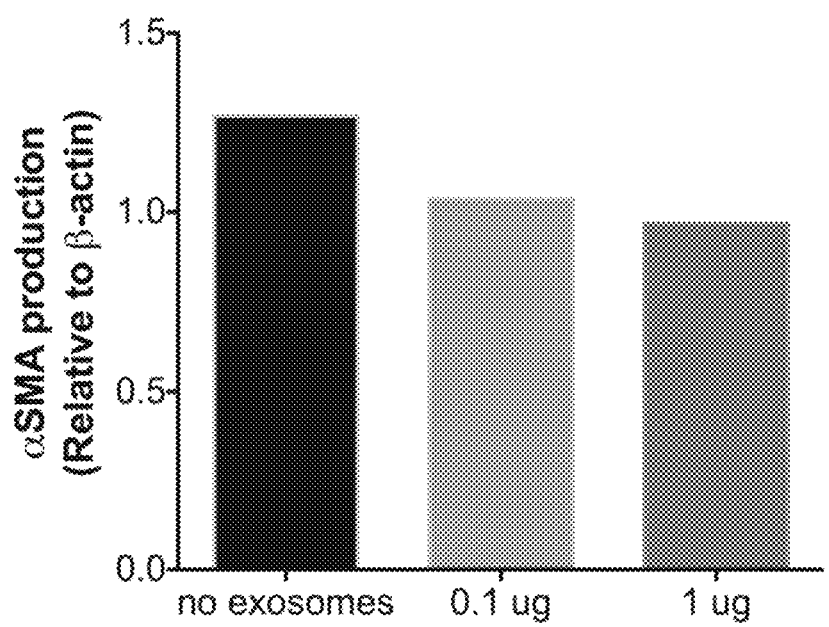
FIG. 7 is a graphical representation showing that amniotic exosomes reverse activation of primary human lung fibroblasts in vitro. When cultured in the presence of 5 mg/mL transforming growth factor β, the exosomes decreased protein levels of α-smooth muscle actin within 24 hours.

Amniotic exosomes directly reverse activation of primary human lung fibroblasts in vitro. When cultured in the presence of 5 ng/mL transforming growth factor β, amniotic exosomes decreased protein levels of α-smooth muscle actin within 24 hours. The results are shown in FIG. 7.

Figure 8A:
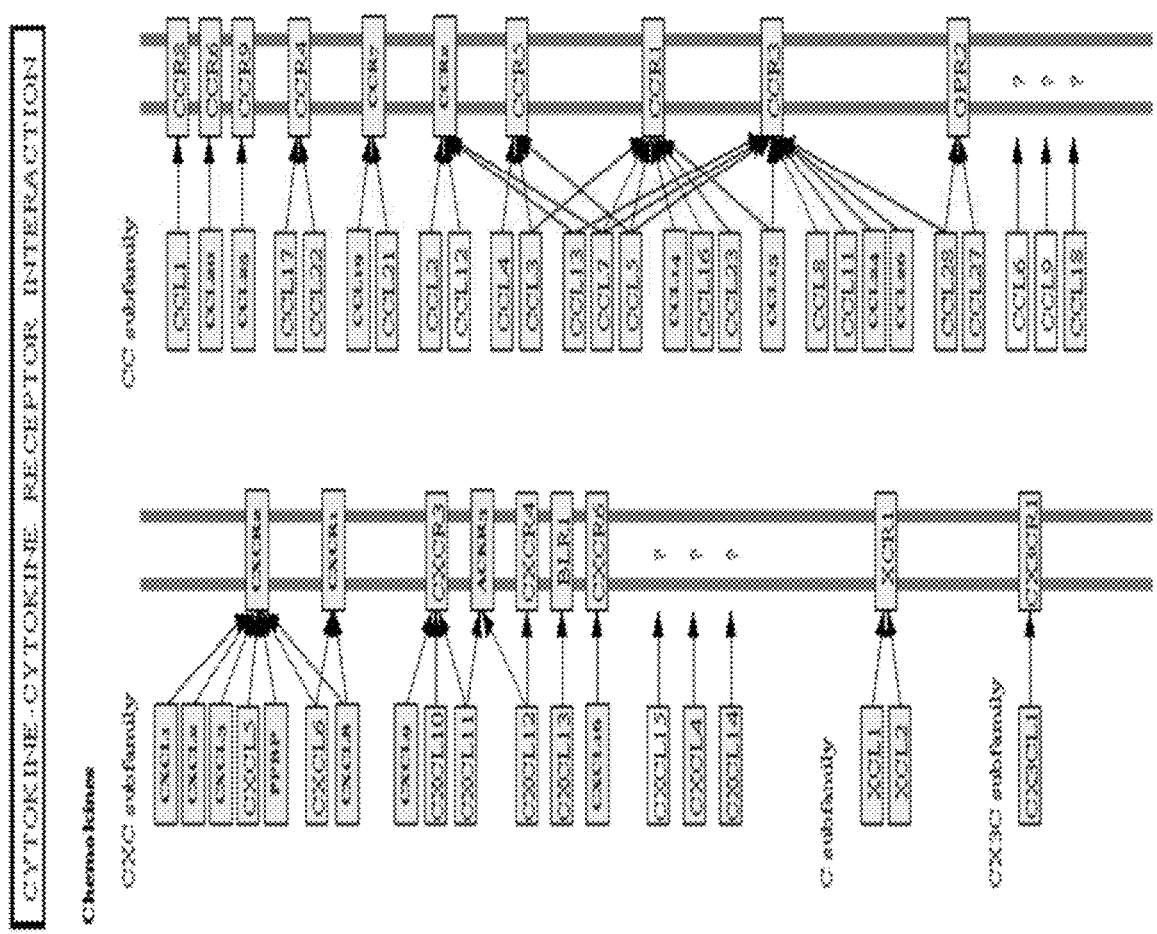
FIG. 8 is a diagrammatic representation showing that amniotic exosomes contain miRNAs that target cytokine-cytokine receptor signaling pathways. Yellow boxes indicate a target by one or more miRNAs.
Figure 8B:
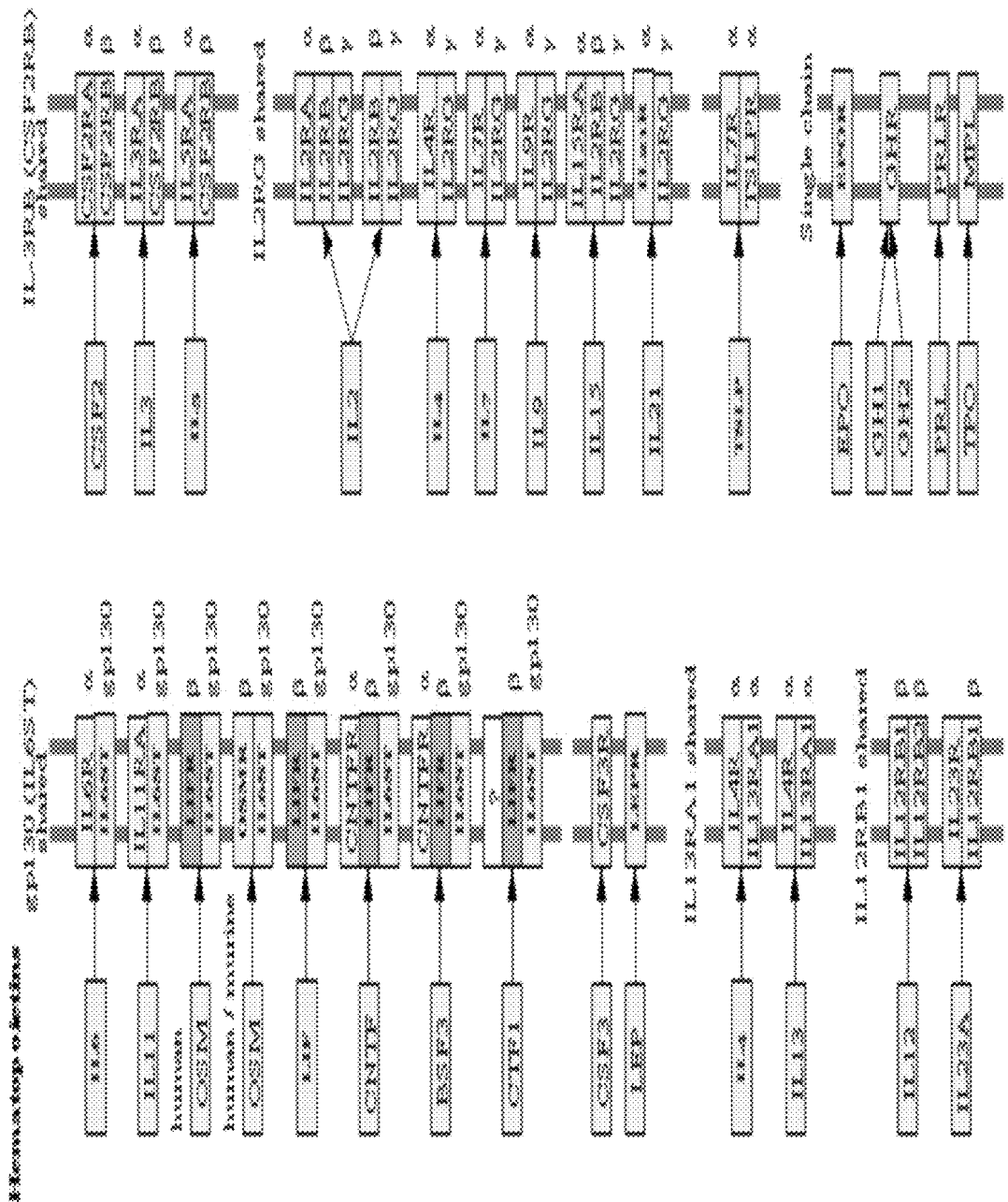

Amniotic exosomes contain miRNAs that target the cytokine-cytokine receptor signaling pathways as shown in FIG. 8, where yellow boxes indicate a target by one or more miRNAs.

Figure 9A:
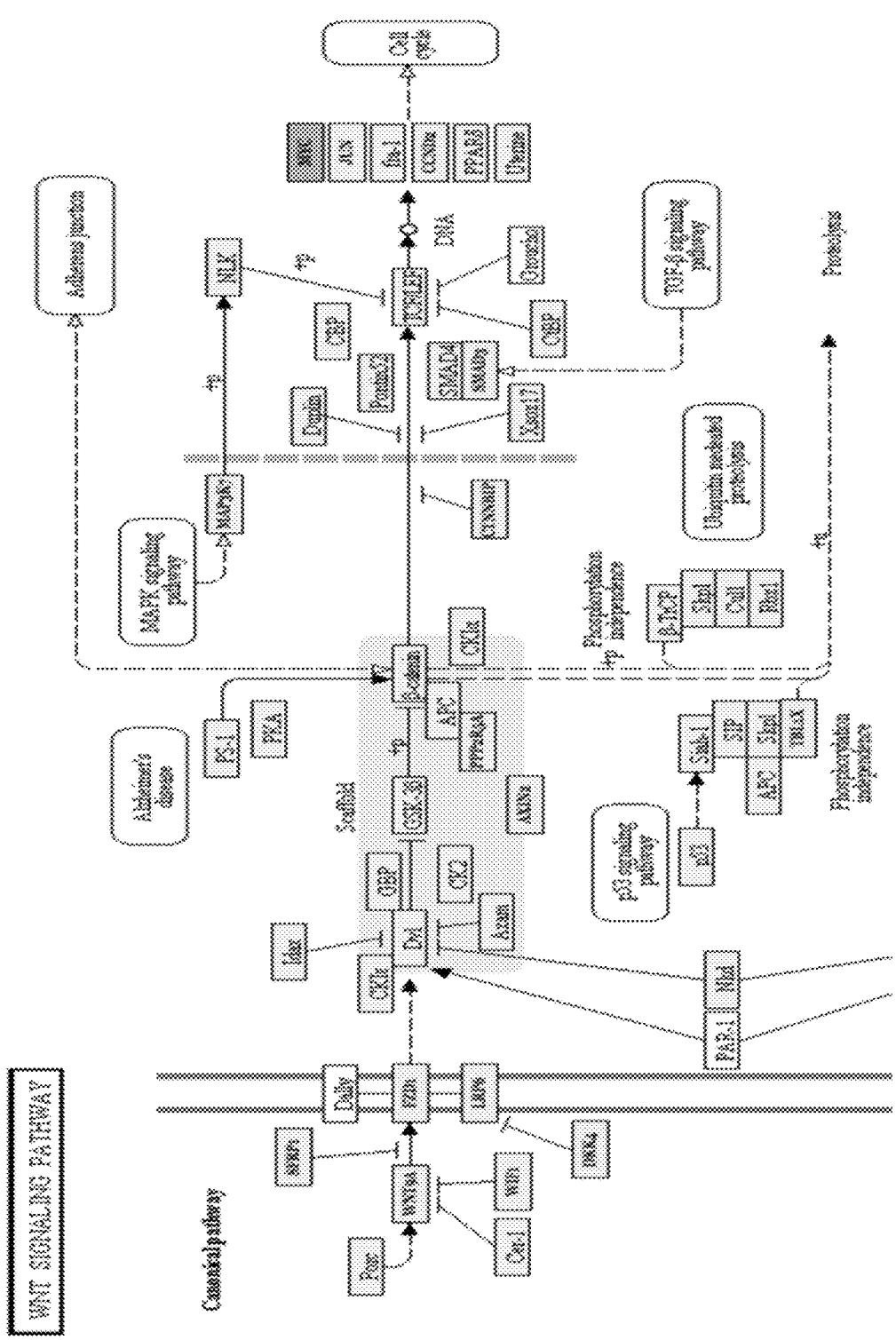
FIG. 9 is a diagrammatic representation showing that amniotic exosomes contain miRNAs that target Wnt signaling pathways. Yellow boxes indicate a target by one or more miRNAs.
Figure 9B:
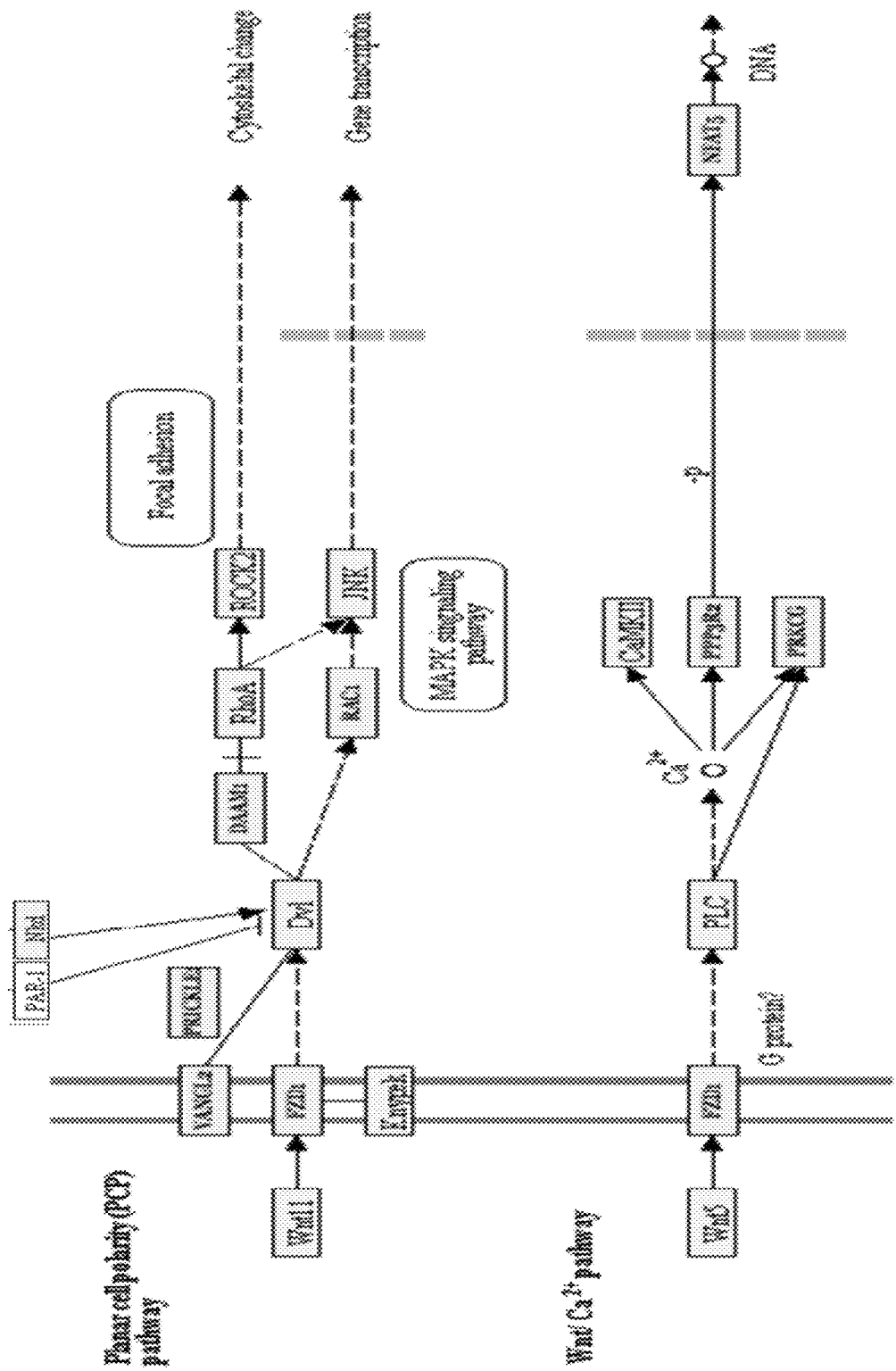

Amniotic exosomes contain miRNAs that target the Wnt signaling pathways as shown in FIG. 9, where yellow boxes indicate a target by one or more miRNAs.

Figure 10:
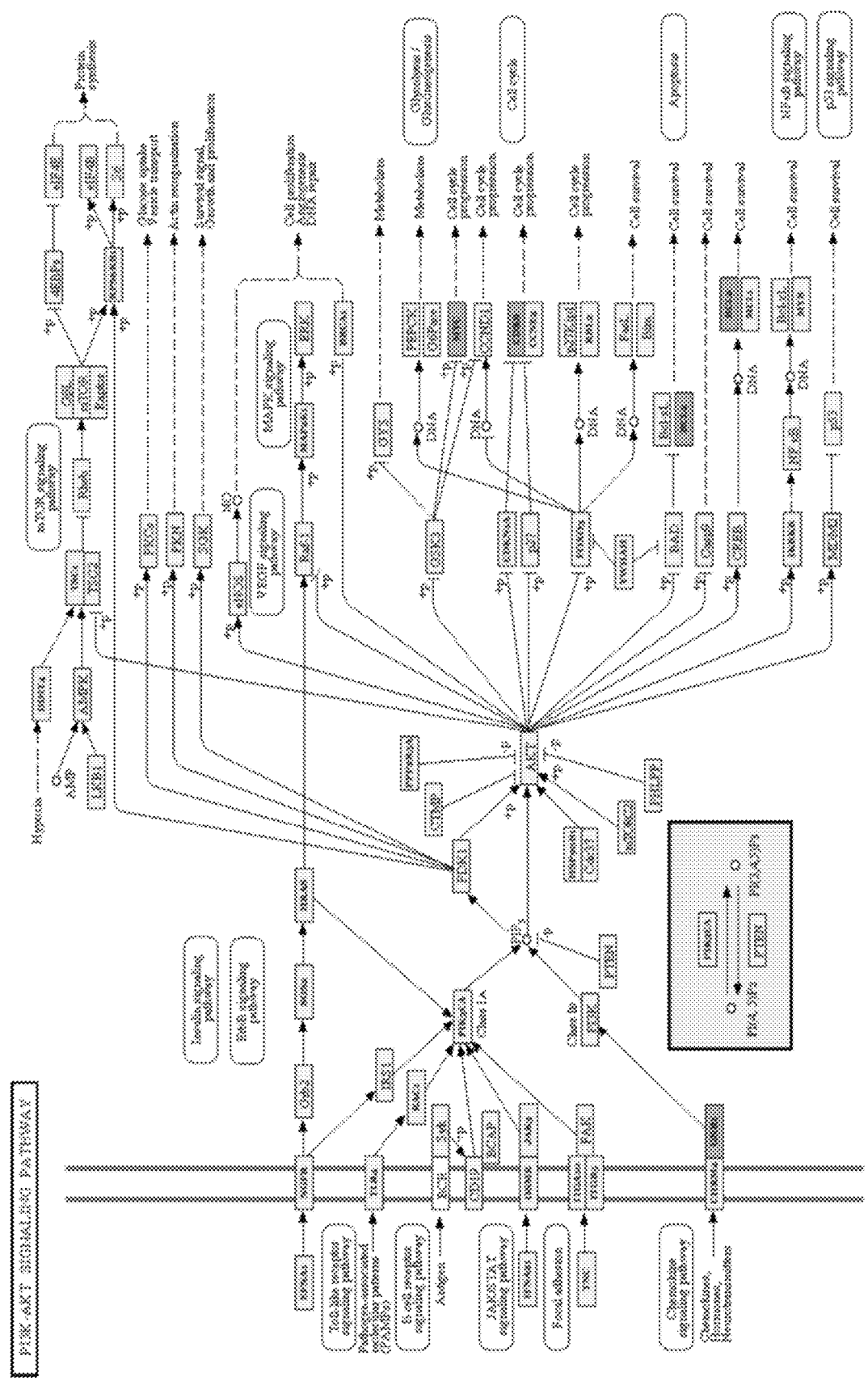
FIG. 10 is a diagrammatic representation showing that amniotic exosomes contain miRNAs that target PI3K-Akt signaling pathways. Yellow boxes indicate a target by one or more miRNAs.

Amniotic exosomes contain miRNAs that target the PI3K-Akt signaling pathways as shown in FIG. 10 where yellow boxes indicate a target by one or more miRNAs.

Figure 11:
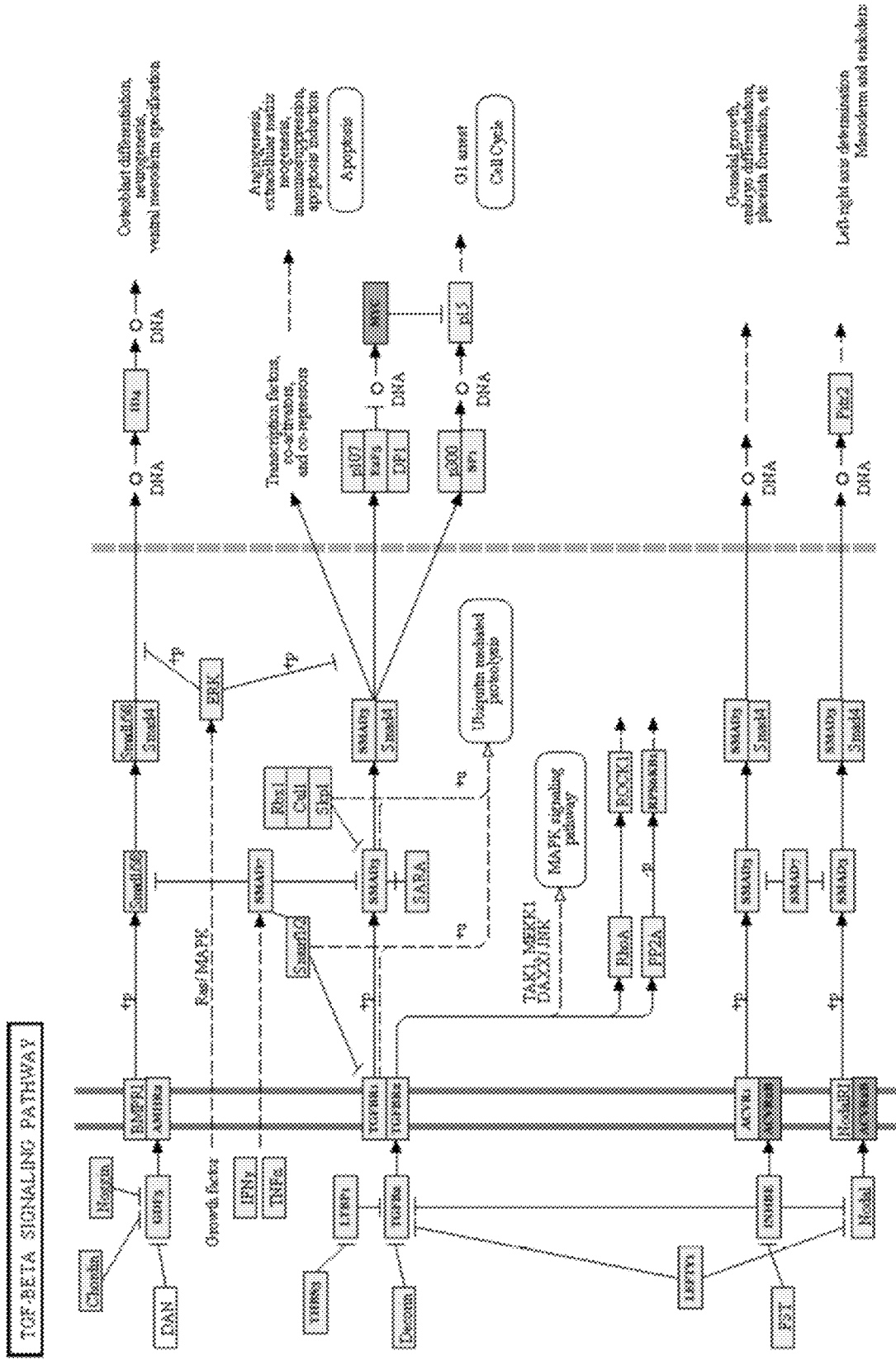
FIG. 11 is a diagrammatic representation showing that amniotic exosomes contain miRNAs target TGFβ signaling pathways. Yellow boxes indicate a target by one or more miRNAs.
Figure 12:
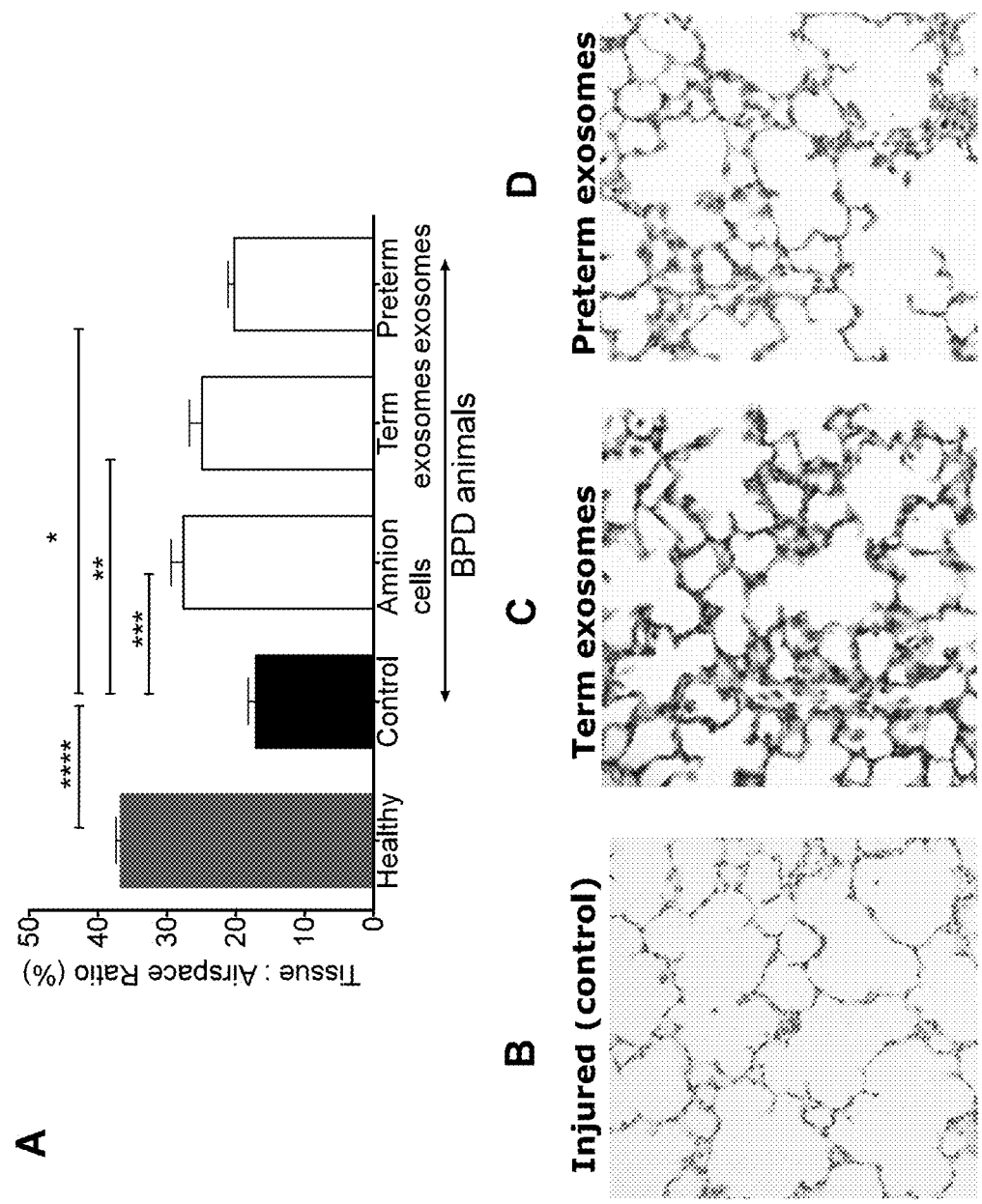
FIG. 12A is a graphical representation and FIGS. 12B, C and D are photographic representations showing the lung regenerative effects of amniotic exosomes comprising tissue airspace ratio (%) between healthy control hAECs, term exosomes and preterm exosomes. A "term" exosome is an exosome isolated from hAEC at the end of a pregnancy. The "preterm" exosome is isolated prior to pregnancy term.

Amniotic exosomes contain miRNAs that target the TGFβ signaling pathways as shown in FIG. 11 where yellow boxes indicate a target by one or more miRNAs.

It is clear that amniotic exosomes are as, if not more, effective than AECs such as hAECs and have a great capacity to induce cellular and molecular repair mechanisms in a diverse range of physiological and neural processes.

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

BIBLIOGRAPHY

Anderson et al. (2016) *Stem Cells.* http://doi.org/10.1002/stem.2298
Doyle et al. (2006) *Paediatrics* 118: 108-113
Egleton and Davis (1997) *Peptides* 18:1431-1439
Fishback et al. (2013) *Sci Transl Med* 5:179 ps7)
Hodges et al. (2012) *Am J Obstet Gynerol* 206: 448e8-448e15
Langer (1990) *Science* 249:1527-1533
Lee et al. (2014) *Cell* 156:440-455
Lim et al. (2013) *Placenta* 34: 486-492
Lodha et al. (2014) *PLoS ONE*: e90843
Putney and Burke (1998) *Nat Biotech* 16:153-157
Remington's Pharmaceutical Sciences (1990), 18th Edition, Mack Publishing Company, Easton, Pa.
Moodley et al. (2010) *Am J Respir Crit Care Med* i:643-651
Murphy et al. (2012) *Cell Transplant* 21:1477-1492
Nold et al *Proc. Natl Acad. Sci USA* 110:14384-14389
Schellenberg et al. (2011) *Aging* (Albany N.Y.) 3:873-888
Sayani and Chien (1996) *Crit Rev Ther Drug Carrier Syst* 13:85-184
Tan et al. (2015) *Stem Cell Res Ther* 6:8
Vosdoganes et al. (2013) *Cytotherapy* 15:1021-1029
Yawno et al. (2013) *Dev Neurosci* 35:272-282

The invention claimed is:

1. A method of treating a human subject who exhibits liver fibrosis or lung fibrosis, the method comprising:
   systemically or locally administering to the human subject an effective amount of mammalian amniotic exosomes derived from allogeneic mammalian amnion epithelial cells derived from a human donor; and
   the amniotic exosomes releasing proteomic and genetic molecules which activate one or more endogenous repair mechanisms selected from reduced T-cell proliferation, increased macrophage phagocytosis, activation of endogenous stem cells, or inhibition of collagen production in activated fibroblasts, to thereby treat liver fibrosis or lung fibrosis in the human subject.

2. The method of claim 1 wherein the amniotic exosomes reverse lung infection and fibrosis and reverse activation of primary lung fibroblasts.

3. The method of claim 1 wherein the amniotic exosomes contain miRNAs which target cytokine-cytokine receptor, Wnt, PI3K-Akt and TGFβ signaling pathways.

4. The method of claim 1 wherein the amniotic exosomes are derived from a bank of immortalized human amnion epithelial cell lines.

5. The method of claim 1 wherein the amniotic exosomes are selected from a bank of lyophilized amniotic exosomes derived from an immortalized human amniotic epithelial cell line.

6. A method for administering amniotic exosomes to a human subject who exhibits liver fibrosis or lung fibrosis to activate one or more endogenous repair mechanisms in the human subject, the method comprising:
   isolating amniotic exosomes from an immortalized amnion epithelial cell line derived from a human donor and systemically or locally administering an effective amount of the isolated amniotic exosomes to the human subject; and
   the amniotic exosomes releasing proteomic and genetic molecules which activate one or more endogenous repair mechanisms selected from reduced T-cell proliferation, increased macrophage phagocytosis, activation of endogenous stem cells, or inhibition of collagen production in activated fibroblasts, to thereby treat liver fibrosis or lung fibrosis in the human subject.

7. The method of claim 6, wherein the amniotic exosomes facilitate repair or regeneration of organ damage following trauma, disease, or substance abuse.

* * * * *